United States Patent [19]

Uchida et al.

[11] Patent Number: 5,151,497

[45] Date of Patent: Sep. 29, 1992

[54] HISTIDYL PEPTIDE DERIVATIVES

[75] Inventors: Itsuo Uchida; Akira Saito; Akihiro Yasuda, all of Yokohama; Kunio Iwata, Hatano; Hiroaki Hari, Tokushima; Katsuyoshi Hara, Yokohama; Mutsuyoshi Matsushita, Hatano; Koretake Anami, Nakatsu; Junichi Haruta, Yokohama; Noboru Furukawa, Hatano, all of Japan

[73] Assignees: Japan Tobacco Inc., Tokyo; Yoshotomi Pharmaceutical Industries, Ltd., Osaka, both of Japan

[21] Appl. No.: 729,415

[22] Filed: Jul. 12, 1991

Related U.S. Application Data

[63] Continuation-in-part of Ser. No. 481,559, Feb. 20, 1990, abandoned, and a continuation-in-part of Ser. No. 517,035, May 1, 1990, abandoned, and a continuation-in-part of Ser. No. 571,099, Aug. 21, 1990, abandoned.

[30] Foreign Application Priority Data

Aug. 17, 1990 [JP] Japan ................................ 2-215752

[51] Int. Cl.$^5$ .......................... A61K 37/02; C07K 5/08
[52] U.S. Cl. ...................................... 530/331; 530/330; 546/16; 546/209; 546/210; 548/147; 548/200; 548/336
[58] Field of Search ................. 530/330, 331; 514/18, 514/19; 546/16, 209, 210; 548/147, 200, 336

[56] References Cited

U.S. PATENT DOCUMENTS

| | | | |
|---|---|---|---|
| 3,959,248 | 11/1975 | Veber | 530/331 |
| 4,045,556 | 8/1977 | Schwertner et al. | 424/177 |
| 4,100,152 | 7/1978 | Fujimo et al. | 530/331 |
| 4,610,821 | 9/1986 | Tamura et al. | 540/200 |
| 4,636,567 | 1/1987 | Tamura et al. | 548/336 |
| 4,788,179 | 11/1988 | Flohe et al. | 514/19 |

FOREIGN PATENT DOCUMENTS

| | | |
|---|---|---|
| 0001845 | 5/1979 | European Pat. Off. . |
| 0171159 | 2/1986 | European Pat. Off. . |
| 60-172996 | 9/1985 | Japan . |
| 61-33197 | 2/1986 | Japan . |
| 61-83182 | 4/1986 | Japan . |
| 61-22797 | 1/1987 | Japan . |
| 1564078 | 4/1980 | United Kingdom . |

OTHER PUBLICATIONS

Bauer et al., Chemical Abstracts, vol. 92 (1980) pp. 825–826 Abstract No. 42368f.
Kalbacher et al., Chemical Abstracts, vol. 84 (1976), p. 503 Abstract No. 3147w.

*Primary Examiner*—Lester L. Lee
*Attorney, Agent, or Firm*—Wenderoth, Lind & Ponack

[57] ABSTRACT

Novel peptide derivatives of the following formula

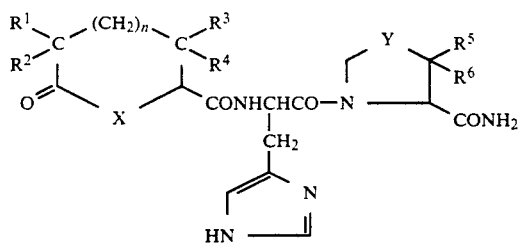

wherein each symbol is as defined in the specification, pharmaceutically acceptable acid addition salts thereof and analogous copounds thereof.

Since the derivatives and their pharmaceutically acceptable acid addition salts of the present invention possess stronger actions on central nervous system (e.g. antagonistic action against hypothermia, locomotor stimulant action, signal reflex stimulant action), they are of use as a therapeutic medicament for central nervous disorders such as impaired consciousness, depression, hypomnesia, the like in association association with schizophrenia, melancholia, senile dementia, sequelae of cerebrovascular disorders, head trauma, epilepsy and spinocerebellar degeneracy.

11 Claims, No Drawings

HISTIDYL PEPTIDE DERIVATIVES

This is a continuation-in-part application of Ser. No. 07/481,559 filed Feb. 20, 1990 (now abandoned), Ser. No. 07/517,035 filed May 1, 1990 (now abandoned) and Ser. No. 07/571,099 filed Aug. 21, 1990 (now abandoned).

BACKGROUND OF THE INVENTION

This invention relates to peptide derivatives of the formulas [I'] to [IV'] to be shown below and pharmaceutically acceptable acid addition salts thereof which exhibit more potent stimulant activities in central nerve system such as an antagonistic action against hypothermia, a locomoter stimulant action, a spinal reflex stimulant action, etc., as compared with other pharmaceuticals, particularly TRH (thyrotropin releasing hormone) and its derivatives, and thus are useful as a therapeutic medicament for central nervous disorders.

As the compounds relevant to the objective compounds of the present invention, known is L-pyroglutamyl-L-histidyl-L-prolinamide (pGlu-His Pro-NH$_2$) referred to as TRH (thyrotropin releasing hormone). TRH is known to have TSH (thyrotropin: thyroid stimulating hormone)-releasing activity and is also known to be useful as a therapeutic medicine for disturbance of consciousness caused by cerebral function disturbances. However, TRH has defects such that it is poorly stable in vivo, easily decomposed by pyroglutamylpeptidase, TRH amidase and other enzymes [Progress of Medicines (Igaku no Ayumi), vol. 134, No. 4, p. 252] and deactivated in a short period, necessitating frequent administration when used, which results in excessive secretion of TSH. For the improvement of the above-mentioned defects of TRH, studies from various aspects have been conducted for TRH derivatives which on the one hand reduce TSH secretion-inducing action as the side effect and on the other hand possess more potent central nerve-stimulant actions such as an antihypnotic action, an anti-reserpine action (antagonistic action against hypothermia), a locomoter stimulant action, a spinal reflex stimulant action, a dopamine potentiating action and an anesthesia antagonism, and have more excellent durability in action than TRH. For example, the following reports have been presented.

U.S. Pat. No. 4,100,152
Japanese Patent Unexamined Publication No. 33197/1986
Japanese Patent Unexamined Publication No. 22797/1987
EP 1845
Japanese Patent Unexamined Publication No. 172996/1985
GB 1564078
U.S. Pat. No. 4,788,179
U.S. Pat. No. 4,636,567
U.S. Pat. Nos. 4,610,821 and 4,299,821

SUMMARY OF THE INVENTION

This invention has been made to improve the above-mentioned defects of TRH, and the object of the present invention is to provide novel peptide derivatives and pharmaceutically acceptable acid addition salts thereof which are useful as a therapeutic medicine for central nervous disturbances, and which possess more potent stimulant actions on central nervous system and long durability than TRH and other known TRH derivatives.

According to the present invention, the novel peptide derivatives and pharmaceutically acceptable acid addition salts thereof are represented by the following formulas [I'] to [IV']:

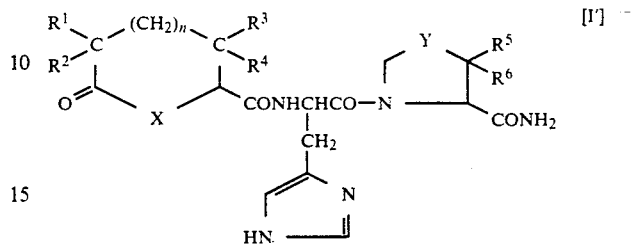

wherein $R^1$ and $R^2$ are the same or different and respectively means a hydrogen atom or a $C_{1-5}$ alkyl group, $R^3$ and $R^4$ are the same or different and respectively mean a hydrogen atom or a $C_{1-5}$ alkyl group or phenyl, or $R^3$ and $R^4$ combinedly means a $C_{2-7}$ alkylene group, $R^5$ and $R^6$ are the same or different and respectively means a hydrogen atom or a $C_{1-5}$ alkyl group, X means —NH— or —O—, Y means —CH$_2$— or —S—, and n means 0 or 1, provided that all of $R^1$, $R^2$, $R^3$ and $R^4$ do not mean a hydrogen atom at the same time,

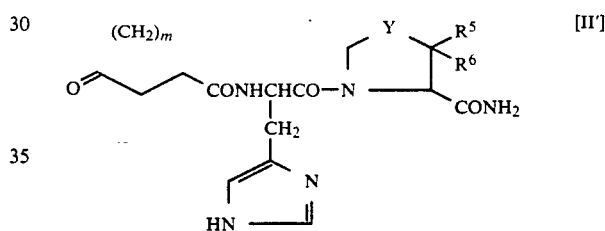

wherein $R^5$ and $R^6$ are the same or different and respectively means a hydrogen atom or a $C_{1-5}$ alkyl group, m is an integer of 1-3 and Y means —CH$_2$— or —S—,

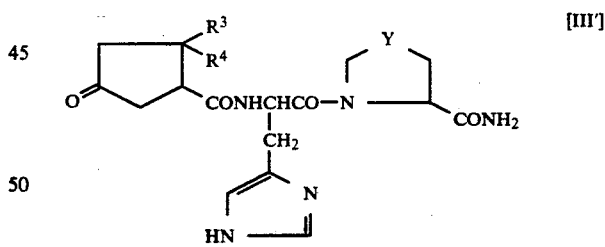

wherein Y means —CH$_2$— or —S—, $R^3$ and $R^4$ are the same or different and respectively means a hydrogen atom or a $C_{1-5}$ alkyl group or phenyl, or $R^3$ and $R^4$ combinedly means a $C_{2-7}$ alkylene group, provided that $R^3$ and $R^4$ do not means a hydrogen atom at the same time,

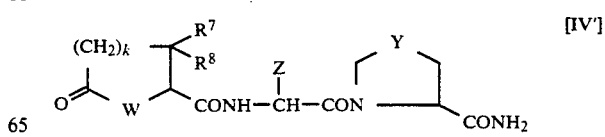

wherein $R^7$ and $R^8$ are the same or different and respectively means a hydrogen atom, a $C_{1-5}$ alkyl group or phenyl, W is —NH— or —CH$_2$—, Z is a hydrogen atom, a benzyl group wherein phenyl may be substituted by hydroxyl, or a C$_{1-5}$ alkyl group which may be substituted by —SH, —SR$^9$, —SO$_2$R$^9$, —CONH$_2$, $$-\underset{R^{11}}{\underset{|}{N}}-R^{10},$$

—OR$^{12}$ or $$-NH-\underset{NH}{\underset{\parallel}{C}}-NH_2,$$

(wherein R$^9$ means a C$_{1-5}$ alkyl group or an aryl group, R$^{10}$ and R$^{11}$ are the same or different and respectively mean a hydrogen atom, a C$_{1-5}$ alkyl group or an amino protecting group and R$^{12}$ is a hydrogen atom, a C$_{1-5}$ alkyl group or a hydroxyl protecting group), Y is —CH$_2$— or —S—, and k is 1 or 2, provided that when W is —NH—, R$^7$ and R$^8$ are not hydrogen atoms at the same time.

Preferred among the compounds of the formula [I'] are derivatives of the following formula [V']

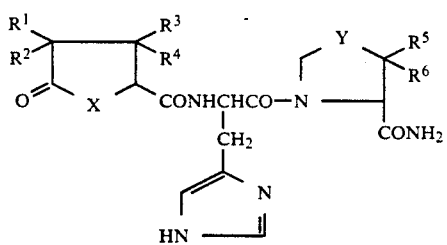

wherein R$^1$, R$^2$, R$^3$, R$^4$, R$^5$, R$^6$, X and Y are as defined in formula [I'], provided that all of R$^1$, R$^2$, R$^3$ and R$^4$ do not mean a hydrogen atom at the same time.

DETAILED DESCRIPTION OF THE INVENTION

In the present specification, the C$_{1-5}$ alkyl group means a straight or branched carbon-chain having, preferably, one through four carbon atoms, which is exemplified by methyl group, ethyl group, propyl group, butyl group, isopropyl group, sec-butyl group, etc. The alkylene group means a bivalent straight aliphatic saturated hydrocarbon having two through seven carbon atoms, preferably two through five carbon atoms, which includes, for example, ethylene group, trimethylene group, tetramethylene group, pentamethylene group, hexamethylene group, heptamethylene group, etc. The alkylene group taken together with the adjacent carbon atom forms a spirocycloalkane. The aryl group means, for example, phenyl, tolyl, etc., the amino protecting group means, for example, acetyl, benzoyl, benzyl, tosyl, benzyloxycarbonyl, tert-butoxycarbonyl, 2,4-dinitrophenyl, etc., and the hydroxyl protecting group means, for example, benzyl, acetyl, benzoyl, etc.

With regard to TRH derivatives, various studies have been conducted as mentioned above, and for example, there have been known TRH derivatives in which the pGlu-moiety of TRH is converted into a heterocyclic group such as

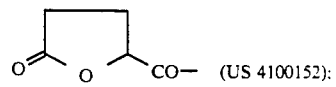 (US 4100152);

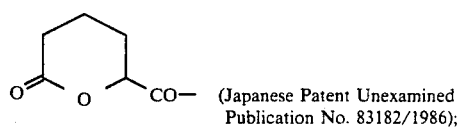 (Japanese Patent Unexamined Publication No. 83182/1986);

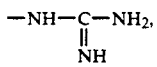 (US 3959248);

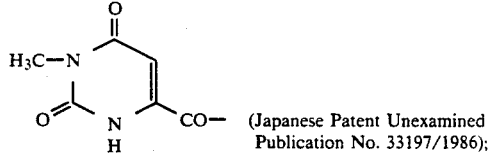 (US 4045556);

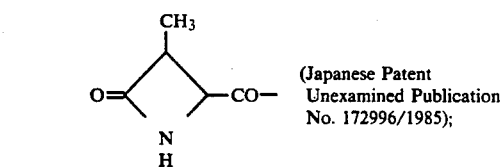 (Japanese Patent Unexamined Publication No. 33197/1986);

 (US 4610821) (US 4636567);

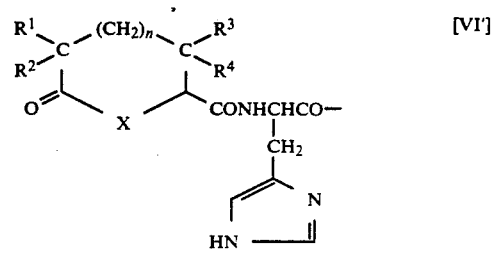 (Japanese Patent Unexamined Publication No. 172996/1985);

or the like. Also, TRH derivatives wherein the His moiety is converted to leucine (Leu) have been reported in U.S. Pat. No. 4,299,821 and others.

Heretofore, however, there have not been made any attempts to convert the pGlu-L-His-moiety of TRH into a structure of the formulas [VI'] to [IX']:

[VI']

wherein n, R$^1$, R$^2$, R$^3$, R$^4$ and X are as defined above,

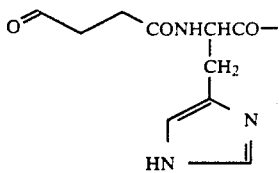 [VII']

wherein m is as defined above,

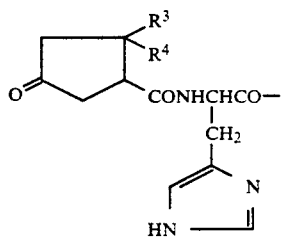 [VIII']

wherein $R^3$ and $R^4$ are as defined above,

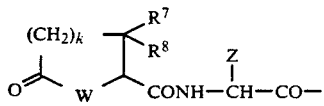 [IX']

wherein k, $R^7$, $R^8$, W and Z are as defined above.

This invention is characterized by the above-mentioned chemical structures, and the conversion into these characteristic structures resulted in enabling of provision of the novel TRH derivatives possessing more potent central nerve stimulant actions and more lasting pharmacological effects than TRH or other known derivatives thereof.

The objective compounds [I'] to [IV'] of this invention are capable of forming pharmaceutically acceptable salts thereof with an acid. Examples of the acid include inorganic acids such as hydrochloric acid and sulfuric acid or organic acids such as citric acid, acetic acid and tartaric acid. These salts are also encompassed in the present invention.

The objective compounds [I'] to [IV'] of the present invention have at least two asymmetric carbons, and there exist stereoisomers based on such asymmetric carbons. The objective compounds of the present invention include respective isolated stereoisomers and the mixtures of the stereoisomers.

According to the present invention, the objective compounds I' to [IV'] or their acid addition salts can be produced by the following methods; for example, the compounds of the formula [I'] or their acid addition salts can be produced by the method below.

(A) A compound of the formula [III]

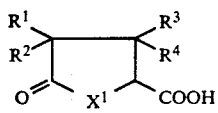 [III]

wherein $R^1-R^4$ are of the same meaning as defined above and $X^1$ means imino group, a protected imino group or an oxygen atom, or a reactive derivative thereof is condensed with a compound of the formula [IV]

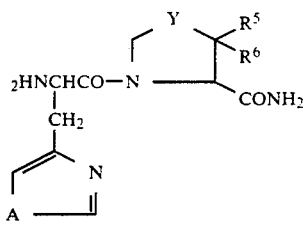 [IV]

wherein A means imino group or a protected imino group and $R^5$, $R^6$ and Y are of the same meaning as defined above, or a salt thereof;

(B) a compound of the formula [V]

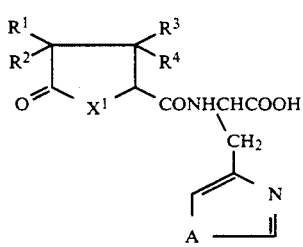 [V]

wherein $R^1-R^4$, $X^1$ and A are of the same meaning, or a salt thereof, or a reactive derivative thereof is condensed with an aminoacid amide of the formula [VI]

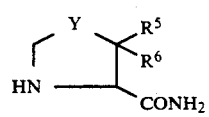 [VI]

wherein Y, $R^5$ and $R^6$ are of the same meaning as defined above, or a salt thereof; or (C) a compound of the formula [VII]

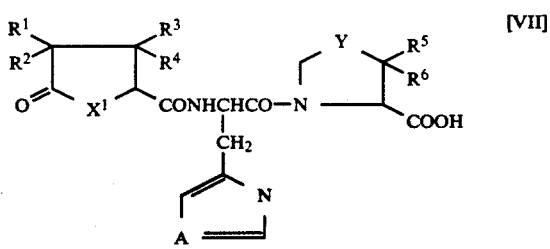 [VII]

wherein $R^1-R^6$, $X^1$, A and Y are of the same meaning as defined above, or a salt thereof, or a reactive derivative thereof is subjected to amidation, and (D) thereafter, when $X^1$ and/or A in the product thus-obtained by the above step (A), (B) or (C) is a protected imino group, the protective group is removed; and (E) whereafter if desired, the thus-obtained product is converted into an acid addition salt thereof, to yield the objective compound.

The starting compounds [IV]-[VII] of the present invention can be subjected to the respective reaction either in the form of free base or in the form of salt. The salt can be preferably used in the form of acid addition salt, and as such acid addition salt, use can be made of, for example, an inorganic acid addition salt such as hydrochloride or hydrobromide, or an organic acid addition salt such as trifluoroacetate or p-toluenesulfonate.

As the reactive derivative of the compounds [III], [V] and [VII], use can be made of an active ester (e.g. N-hydroxysuccinimido ester, pentachlorophenyl ester, N-hydroxybenzotriazole ester), an acid halide (e.g. acid chloride), an acid azido, an acid anhydride, imidazolamide, etc., corresponding to the respective compounds. The active ester may be subjected to peptide-synthesizing reaction after isolated or without being isolated. As the reactive derivative of the compound [VII], use can be preferably made of, for example, an ester (an alkyl ester such as ethyl ester or methyl ester; an aralkyl ester such as benzyl ester, etc.) or the like.

When the group $X^1$ and/or A in the above-mentioned starting compounds [III], [IV], [V] and [VII] are (is) a protected imino group, use can be made of any protective group conventionally used in peptide synthesis as the protective group of the imino group. Examples of the suitable protective group include benzyloxycarbonyl group, benzyl group, tosyl group, tert-butoxycarbonyl group and 2,4-dinitrophenyl group.

Reaction Steps (A) and (B)

Both of the condensation reaction of a compound [III] or a reactive derivative thereof with a compound [IV] or a salt thereof and the condensation reaction of a compound [V] or a salt thereof or a reactive derivative thereof with a compound [VI] or a salt thereof, which are peptide synthetic reactions, can be carried out by a conventional means. For example, the condensation reaction of a compound [III] with a compound [IV] or a salt thereof and that of a compound [V] or a salt thereof with a compound [VI] or a salt thereof can be carried out in a suitable solvent in the presence of a condensing agent. Examples of the suitable condensing agent include dicyclohexylcarbodiimide, 1-ethyl-3-(3-dimethylaminopropyl)carbodiimide, phosphorus oxychloride, phosphorus trichloride, thionyl chloride, oxalyl chloride, triphenylphosphine and Vilsmeier Reagent. The condensation reaction is carried out preferably at $-50°-50°$ C. When a salt of a compound [IV] is used, the reaction is conducted in the presence of a deacidifying agent.

On the other hand, the condensation reaction of a reactive derivative of a compound [III] with a compound [IV] or a salt thereof and that of a reactive derivative of a compound [V] with a compound [VI] or a salt thereof can be carried out in a suitable solvent in the presence or absence of a deacidifying agent. As the deacidifying agent, mention can be made of, for example, trialkylamines (triethylamine, trimethylamine, etc.), N,N-dialkylanilines (N,N-dimethylaniline, N,N-diethylaniline, etc.), pyridine, N-alkylmorpholines (N-methylmorpholine, etc.), alkali metal hydroxides (potassium hydroxide, sodium hydroxide, etc.), alkali metal carbonates (potassium carbonate, etc.), alkali metal hydrogencarbonates (sodium hydrogencarbonate, etc.) and the like. This condensation reaction can be suitably carried out at $-50°-50°$ C., particularly $-10°-10°$ C.

As the solvent for the condensation reaction usable in the reaction steps (A) and (B), use can be made of, for example, N,N-dimethylformamide, dichloromethane, dioxane, tetrahydrofuran, acetonitrile, ethyl acetate, pyridine, acetone, water, etc.

Reaction Step (C)

The amidation reaction of a compound [VII], a salt thereof or a reactive derivative thereof can be carried out by reacting the compound with ammonia or an ammonia-donating compound. For example, the amidation reaction of a compound [VII] or a salt thereof with ammonia or an ammonia-donating compound can be preferably carried out in the presence of a dehydrating agent in a suitable solvent. As the dehydrating agent, use can be made of, for example, any compound mentioned above as the suitable condensing agent. As the ammonia-donating compound, use can be made of any compound capable of releasing ammonia in the reaction mixture, which is exemplified by ammonium chloride, ammonium carbonate, etc. The amidation reaction is preferably carried out at $-20°$ C.$-20°$ C. As the suitable solvent, mention can be made of, for example, N,N-dimethylformamide, dimethylsulfoxide, tetrahydrofuran, etc. Furthermore, the amidation reaction of a reactive derivative of a compound [VII] or a salt thereof with ammonia or an ammonia-donating compound can be carried out in the presence or absence of a deacidifying agent in a suitable solvent. As the deacidifying agent, use can be made of any of the deacidifying agents mentioned in the description of the above reaction steps (A) and (B). The amidation reaction is preferably carried out at $-20°$ C.$-20°$ C. As the suitable solvent, mention can be made of methanol, ethanol, N,N-dimethylformamide, dimethylsulfoxide and the like.

Reaction Step D

When $X^1$ and/or A in the compound produced in the above-mentioned reaction step (A), (B) or (C) are (is) a protected imino, the deprotection of the protective group can be carried out easily, depending upon the species of the protective group, in accordance with a conventional method such as catalytic reduction, electrolytic reduction, acid treatment, base treatment or oxidation reaction.

Reaction Step (E)

The thus-obtained objective compound can be, if necessary, converted into an acid addition salt easily by treating with a stoichiometric amount of an acid in accordance with a conventional method.

In the above-mentioned reactions, the staring compounds [III]-[VII], the intermediate products and the objective compounds contain 1-6 asymmetric carbon atom(s), and the above methods of the present invention can be carried out using the respective optically active isomers of the starting compounds [III]-[VII] or their respective mixture. Since the above-mentioned reactions of the present invention can be carried out without involving racemization, the intermediate products and the objective compounds can be obtained in the form of the corresponding optically active isomer when the respective optically active isomers of the starting compounds [III]-[VII] are used.

The compounds of the formulas [II'], [III'] and [VI'], or acid addition salts thereof can be produced in the same manner as above except that the following compounds are used as a starting material. In the case of producing compounds of the formula [II'], a compound of the formula [VIII]

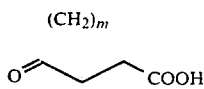   [VIII]

wherein m is as defined above, or its reactive derivative is used in place of a compound of the formula [III]; a compound of the formula [IX]

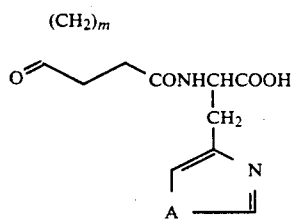   [IX]

wherein m and A are as defined above, or its salt or its reactive derivative is used in place of a compound of the formula [V]; and a compound of the formula [X]

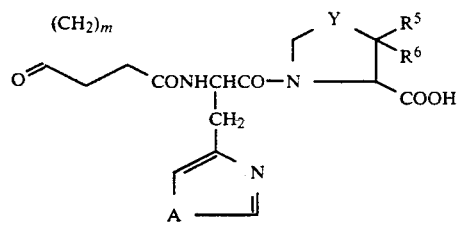   [X]

wherein m, $R^5$, $R^6$, Y and A are as defined above, or its salt or its reactive derivative is used in place of a compound of the formula [VII].

In the case of producing compounds of the formula [III'], a compound of the formula [XI]

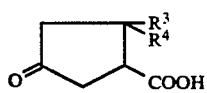   [XI]

wherein $R^3$ and $R^4$ are as defined above, or its reactive derivative is used in place of a compound of the formula [III]; a compound of the formula [XII]

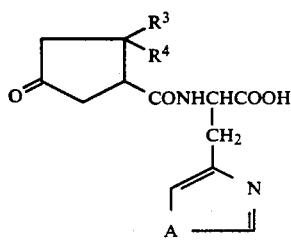   [XII]

wherein $R^3$, $R^4$ and A are as defined above, or its salt or its reactive derivative is used in place of a compound of the formula [V]; and a compound of the formula [VII]

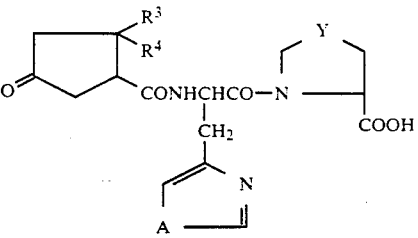   [XIII]

wherein $R^3$, $R^4$, Y and A are as defined above, its salt or its reactive derivative is used in place of a compound of the formula [VII].

In the case of producing compounds of the formula [IV'], a compound of the formula [XIV]

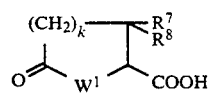   [XIV]

wherein $R^7$, $R^8$ and k are as defined above and $W^1$ is imino group, a protected imino group or methylene group, or its reactive derivative is used in place of a compound of the formula [III]; a compound of the formula [IV]

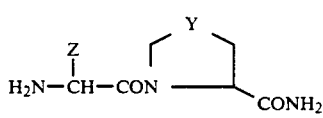   [XV]

wherein Y and Z are as defined above, or its salt is used in place of a compound of the formula [IV]; a compound of the formula [XVI]

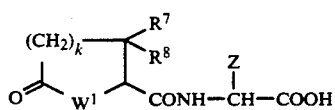   [XVI]

wherein $R^7$, $R^8$, $W^1$, Z and k are as defined above, its salt or its reactive derivative is used in place of a compound of the formula [V]; and a compound of the formula [XVII]

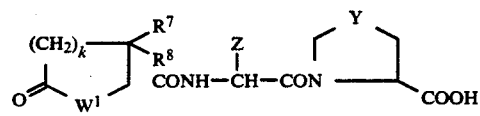   [XVII]

wherein $R^7$, $R^8$, $W^1$, Y, Z and k are as defined above, its salt or its reactive derivative is used in place of a compound of the formula [VII].

The objective compounds [I'] to [IV'] and pharmaceutically acceptable acid addition salts thereof can be administered orally or nonorally as they are or in the form of, for example, powders, granules, tablets, capsules, injections (intravenous, subcutaneous, intramuscular) or suppositories suitably in admixture with pharmacologically acceptable carriers, excipients and diluents.

While the dosage of the objective compounds [I'] to [IV'] or their pharmaceutically acceptable acid addition salts of the present invention varies depending on the administration route, the age, body weight or symptom of the patient and the like, generally it is preferably 0.5 μg-5 mg/kg/day. Particularly, in the case of oral administration, the dosage is preferably 10 μg-5 mg/kg/day and in the case of parenteral administration (e.g. intravenous administration, intramuscular administration, subcutaneous administration), the dosage is preferably 1-1000 μg/kg/day.

Since the compounds [I'] to [IV'] or their pharmaceutically acceptable acid addition salts of the present invention possess more potent actions on central nervous system (e.g. antagonistic action against hypothermia, locomotor stimulant action, spinal reflex stimulant action), they are of use as a therapeutic medicament for central nervous disorders such as impaired consciousness, depression, hypomnesia, the like in association with schizophrenia, melancholia, senile dementia, sequelae of cerebrovascular disorders, head trauma, epilepsy, and spinocerebellar degeneracy.

Below, the present invention is in further detail described by illustrating reference examples and working examples. The abbreviations used in the examples stand for the following meanings respectively.

NMR nuclear magnetic resonance spectra ($^1$H-NMR)
SIMS secondary ion mass spectra
EIMS electronimpact mass spectra
CIMS chemical ionization mass spectra
DMF N,N-dimethylformamide
HOBT 1-hydroxy-1,2,3-benzotriazole
DCC 1,3-dicyclohexylcarbodiimide
THF tetrahydrofuran
WSC 1-(3-dimethylaminopropyl)-3-ethylcarbodiimide The compound which contains the symbol $N^{im}$ in the compound name is the mixture of the compound substituted at the $\pi$ nitrogen atom

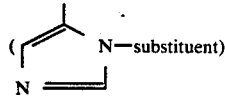

and the compound substituted at the $\tau$ nitrogen atom

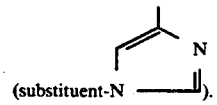

Hydrobromide of dipeptide of the formula [XV] which is used in the present invention was synthesized by the method of T. Szirtes et al [T. Szirtes et al, *J. Med. Chem.*, 27, 741 (1984)].

REFERENCE EXAMPLE 1 cis 2-Methyl-4-oxocyclopentanecarboxylic acid

In acetonitrile (5 ml) were dissolved methyl cis-2-methyl-4-oxocyclopentanecarboxylate [K. Kojima et al., *Chem. Pharm. Bull.*, 33, 2750 (1985)] (827 mg) and sodium iodide (3.175 g), and trimethylchlorosilane (2.69 ml) was added to the solution at room temperature. The mixture was refluxed under nitrogen atmosphere for one day. After the temperature was cooled to room temperature, water was added and the mixture was extracted with ether, followed by washing with an aqueous solution of sodium thiosulfate. The water layer was further extracted with ether. The organic layers were combined, dried over magnesium sulfate and concentrated to dryness. The residue was subjected to silica gel column chromatography with ethyl acetate:chloroform (1:1), and the eluted fractions were combined and concentrated to dryness to yield the title compound (243 mg).

NMR (CDCl$_3$): δppm: 1.14 (3H, d, J=7.0Hz), 2.18 (1H, ddd, J=18.3Hz, 7.8Hz, 1.6Hz), 2.34-2.47 (2H, m), 2.63 (1H, ddd, J=18.3Hz, 6.0Hz, 1.6Hz), 2.74 (1H, m), 3.23 (1H, m).

REFERENCE EXAMPLE 2 trans-2-Methyl-4-oxocyclopentanecarboxylic acid

Methyl trans-2-methyl-4-oxocyclopentanecarboxylate [K. Kojima et at., *Chem. Pharm. Bull.*, 33, 2750 (1985)] (495 mg) was dissolved in methanol (3 ml), and a 1N aqueous solution of sodium hydroxide (3.5 ml) was added to the solution at 0° C. After the mixture was stirred at room temperature for 1 hour, it was acidified with dilute hydrochloric acid, followed by extraction with ether. The extract was concentrated to dryness and the residue was subjected to silica gel column chromatography with ethyl acetate-chloroform (1:1) as eluent, and the eluted fractions were combined and concentrated to dryness to afford the title compound (219 mg) as crystals.

NMR (CDCl$_3$): δppm: 1.26 (3H, d, J=6.4Hz), 1.94 (1H, m), 2.45-2.65 (4H, m), 2.74 (1H, m).

REFERENCE EXAMPLE 3

1,4,4-Tricarboethoxy-3-oxospiro[4.5]decane

Diethyl cyclohexylidenemmalonate [W. Lehnert, *Tetrahedron*, 29, 635 (1973)] (3.1 g) and 1,4-bis(trimethylsiloxy)-1,4-diethoxy-1,3-butadiene [N. R. Long et al, *Synthetic Commun.*, 11, 687 (1981)] (5 g) were dissolved in dry dichloromethane (40 ml), and 15.7 ml of a 1.0M solution of titanium (IV) chloride in dichloromethane was added to the solution at room temperature under nitrogen atmosphere. After the mixture was stirred at room temperature for 8 hours, 25 ml of a 10% aqueous solution of sodium hydrogen carbonate was added and the organic layer was separated, dried over magnesium sulfate and concentrated to dryness. The residue was subjected to silica gel column chromatography with hexane-ethyl acetate (5:1) as eluent, and the eluted fractions were combined and concentrated to dryness to afford the title compound (990 mg).

NMR (CDCl$_3$): δppm: 1.18-1.37 (9H, m), 1.42-1.82 (10H, m), 2.62 (1H, dd, J=8.7Hz and 19.1Hz), 3.01 (1H, dd, J=4.9Hz and 19.1Hz), 3.36 (1H, dd, J=4.9Hz and 8.7Hz), 4.07-4.32 (6H, m).

IRγ (CHCl$_3$) cm$^{-1}$: 1771 and 1726.

REFERENCE EXAMPLE 4

1-Carboxy-3-oxospiro[4.5]decane 1,4,4-Tricarboethoxy-3-oxospiro[4.5]decane (990 mg), water (196 μl) and lithium chloride (350 mg) were dissolved in dimethylsulfoxide (25 ml), and the mixture was stirred at 170° C. for 4 hours. After cooling to room temperature, saturated brine (40 ml) was added and the mixture was extracted with ethyl acetate. The organic layer was separated, dried over magneium sulfate and concentrated to dryness. The residue was purified through silica gel column chromatography (hexane-ethyl acetate=5:1) to give pure 1-carboethoxy-3-oxospiro[4.5]decane (450 mg), which was added to 5N hydrochloric acid (20 ml), and the mixture was refluxed for 3 hours. After cooling to room temperature, the mixture was concentrated and the residue was adjusted to pH 10 with aqueous solution of sodium hydroxide, followed by washing with ether. The aqueous layer was acidified with 5N hydrochloric acid to pH 2, followed by extraction with ether. The ethereal solution was dried, and concentrated to dryness to afford the title compound (310 mg) as colorless crystals.

NMR (CDCl$_3$): m.p. 146°–147° C.

δppm: 1.20–1.80 (10H, m), 2.15 (1H, d, J=18.2Hz), 2.41–2.71 (3H, m), 2.93 (1H, dd, J=6.1Hz and 8.0Hz).

REFERENCE EXAMPLE 5

2-Aza-4-carboethoxy-1 carbomethoxy-3-oxospiro[4.5]decane

Diethyl cyclohexylidenemalonate (7.0 g) was dissolved in dry dichloromethane (300 ml), and 34.96 ml of a 1.0M solution of titanium (IV) chloride in dichloromethane was added to the solution at room temperature under nitrogen atmosphere. After the mixture was stirred for 30 min., a solution of 2-[(2,2,2-trifluoro-1-trimethylsiloxy)ethylideneimino]-1-methoxy-1-trimethylsiloxy ethylene (T. Oesterle et al, *Synthesis*, 1985, 403) (19.2 g) in dichloromethane (20 ml) was added to the solution at room temperature. After the mixture was stirred for 15 hours, a diluted aqueous solution of sodium hydrogen carbonate was added to the mixture at 0° C. and the organic layer was separated. The aqueous layer was extracted with dichloromethane. The extract was dried over magnesium sulfate and concentrated. The residue was subjected to silica gel column chromatography with ethyl acetate—chloroform (1:3) as eluent, and the eluted fractions were combined and concentrated to dryness to give the title compound (3.29 g).

NMR (CDCl$_3$): δppm: 1.30 (3H, t, J=7Hz), 1.00–2.00 (10H, m), 3.41 (1H, s), 3.80 (3H, s), 4.23 (2H, q, J=7Hz), 4.33 (1H, s).

IRγ (neat) cm$^{-1}$: 3220, 1736, 1717.

REFERENCE EXAMPLE 6

2-Aza-1-carboxy-3 oxospiro[4.5]decane

2-Aza-4-carboethoxy-1-carbomethoxy-3-oxospiro[4.5]decane (500 mg) was dissolved in 6N hydrochloric acid (10 ml) and the mixture was refluxed for 1 hour. After the mixture was concentrated, the residue was heated at 150°–160° C. for 30 minutes. After cooling to room temperature, water was added and washed with ethyl acetate. The aqueous layer was concentrated to dryness to afford the title compound (173 mg).

NMR (CD$_3$OD): δppm: 1.20–1.80 (10H, m), 2.22 (1H, d, J=17Hz), 2.34 (1H, d, J=17Hz), 3.88 (1H, s).

IRγ (neat) cm$^{-1}$: 3300, 1723, 1649.

REFERENCE EXAMPLE 7 cis-2-Ethyl-4-oxocyclopentanecarboxylic acid

The crude methyl 1,2-cis-2-ethyl-3-methoxycarbonyl-4-oxocyclopentanecarboxylate was obtained from methyl propionyl-acetate (26 g) and methyl 4-bromoacetate (19.5 g) according to the literature procedure [L. J. Dolby et al., *J. Org. Chem.*, 33, 4508 (1968)]. The crude compound was dissolved in 3N-hydrochloric acid (250 ml), then refluxed for 2 hours. The mixture was concentrated to dryness. The residue was distilled under reduced pressure to give cis-2-ethyl-4-oxocyclopentanecarboxylic acid (9.4 g).

NMR (CDCl$_3$): δppm: 1.01 (3H, t, J=7.4Hz), 1.33–1.52 (1H, m), 1.54–1.71 (1H, m), 2.12–2.65 (5H, m), 3.19–3.31 (1H, m).

IVγ (CHCl$_3$) cm$^{-1}$: 1744 and 1707.

bp: 151°–153° C./2.5 mmHg.

REFERENCE EXAMPLE 8

3-Methyl-6-oxo-2-piperidinecaboxylic acid

3-Methyl-2-piperidinecarboxylic acid [S. R. Angle, D. O. Arnaiz, *Tetrahedron Lett.*, 30, 515 (1989)] (1.514 g), N,N-dimethylaminopyridine (0.2 g) and di-t-butyldicarbonate (4 g) were dissolved in methanol-containing acetonitrile (20 ml), and the mixture was stirred at room temperature overnight. 5% Citric acid was added thereto, and the mixture was extracted with ether, followed by drying, concentration and purification by silica gel column chromatography using hexane-ethyl acetate (7:3) to give 400 mg of an ester compound. The ester compound, ruthenium trioxide (6 mg) and sodium periodate (2 g) were dissolved in a two-layer solvent of ethyl acetate (10 ml) and H$_2$O (20 ml), followed by stirring overnight. The mixture was extracted with ethyl acetate, dried and concentrated, after which it was purified by silica gel column chromatography to give 255 mg of an amide compound. This amide compound was dissolved in trifluoroacetic acid (10 ml) and the mixture was stirred overnight. The solvent was distilled off, and 1N NaOH (1 ml) was added thereto. The mixture was stirred at room temperature for 10 minutes. After acidifying the mixture with diluted hydrochloric acid, it was concentrated and extracted with ethyl acetate. The solvent was distilled off to give 30 mg of 3-methyl-6-oxo-2-piperidinecarboxylic acid.

NMR (CD$_3$OD): δppm: 1.0–1.3 (m, 3H), 1.5–2.1 (m, 2H), 2.2–2.6 (m, 3H), 3.75 (d, J=6Hz), 0.5H), 4.10 (d, J=4Hz), 0.5H).

EXAMPLE 1

N$^\alpha$-(cis-3-Methylpyroglutamyl)-L-histidyl-L-prolinamide (Compound 1)

L-Histidyl-L-prolinamide dihydrobromide (4.33 g) was dissolved in DMF (15 ml), and triethylamine (2.92 ml) was added to the solution under cooling at <10° C. After the mixture was stirred under ice-cooling for 10 minutes, the resulting precipitation was filtered off to give a DMF solution of L-histidyl-L-prolinamide, which was immediately used in the following synthetic reaction.

cis-3-Methylpyroglutamic acid [A. B. Mauger, *J. Org. Chem.* 46, 1032 (1981)] (1.5 g) was dissolved in DMF (30 ml), and HOBT (1.6 g) was added to the solution, followed by addition of DCC (2.81 g) under cooling at 0° C. The mixture was stirred at the same temperature overnight. The above-mentioned DMF solution of L-histidyl-L-prolinamide was added to the mixture, and the mixture was stirred at 5° C. overnight. After the resulting precipitation was filtered off, the filtrate was concentrated to dryness under reduced pressure and the residue was subjected to silica gel column chromatography with chloroform-methanol-ammonia water (40:10:1) as eluent. The eluted fractions were combined and concentrated to dryness to give N$^\alpha$-(cis-3-methylpyroglutamyl)-L-histidyl-L-prolinamide (2.2 g) as powders.

NMR (CD$_3$OD): δppm: 0.88 (1.5H, d, J=7.0Hz), 0.96 (1.5H, d, J=7.0Hz), 1.80–2.16 (4H, m), 2.16–2.47 (2H, m), 2.78 (1H, m), 3.09 (1H, m), 3.18 (1H, m), 3.52

(1H, m), 3.88 (1H, m), 4.22 (1H, m), 4.44 (1H, m), 4.90–5.00 (1H), 7.18 (1H, s), 8.04 (0.5H, s), 8.09 (0.5H, s).
SIMS m/z: 377 (M+1)$^+$.

EXAMPLE 2

N$^\alpha$-(trans-3-Methylpyroglutamyl)-L-histidyl-L-prolinamide (Compound 2)

In the same manner as in Example 1, from trans-3-methylpyroglutamic acid [A. B. Mauger, *J. Org. Chem.*, 46, 1032 (1981)] (200 mg) and L-histidyl-L-prolinamide dihydrobromide (578 mg), N$^\alpha$-(trans-3-methylpyroglutamyl)-L-histidyl-L-prolinamide (223 mg) was obtained as powders.

NMR (CD$_3$OD): δppm: 1.14 (1.5H, d, J=7.0Hz), 1.20 (1.5H, d, J=7.0Hz), 1.77–2.10 (4H, m), 2.10–2.60 (3H, m), 3.00 (1H, m), 3.12 (1H, dd, J=14.4Hz and 7.0Hz) 3.37 (1H, m), 3.70–3.85 (2H, m), 4.41 (1H, m), 4.80–5.00 (1H), 6.90 (0.2H, s), 6.97 (0.8H, s), 7.62 (1H, s).
SIMS m/z: 377 (M+1)$^+$.

EXAMPLE 3

3-[N$^\alpha$-(cis-3-Methylpyroglutamyl)-L-histidyl]-L-thiazolidine-4-carboxamide (Compound 3)

3-(N$^{im}$-Tosyl-L-histidyl)-L-thiazolidine-4-carboxamide.hydrochloride [Itsuro Sobue, et al, Japanese Patent Unexamined Publication No. 190795/1985] (500 mg), cis-3-methylpyroglutamic acid (234 mg) and HOBT (249 mg) were dissolved in a mixture of DMF (5 ml) and THF (5 ml), and WSC.hydrochloride (230 mg) was added to the solution while stirring under cooling at −10° C. Thereto was added triethylamine (227 μl), and after the pH was adjusted to pH 5, the mixture was stirred at room temperature for 2 days. After the resultant precipitation was filtered off, the filtrate was concentrated under reduced pressure to dryness. The residue was subjected to purification by HP-20 column chromatography (1.0×40 cm). Washing with water and eluting with a mixture of water-acetone (1:1) was conducted in order, and the eluted fractions were concentrated under reduced pressure to dryness, and the obtained residue was further purified by silica gel column chromatography with chloroform-methanol-ammonia water (40:10:1) as eluent. From the fractions containing the objective compound 3-[N$^\alpha$-(cis-3-methylpyroglutamyl)-L-histidyl]-L-thiazolidine-4-carboxamide (120 mg) was obtained.

NMR (CD$_3$OD): δppm: 0.83–1.10 (3H), 1.08 (1H, m), 2.35 (1H, m), 2.79 (1H, m), 3.01 (1H, m), 3.10–3.25 (2H, m), 3.32 (1H), 4.14 (1H, t, J=7.0Hz), 4.44 (1H, t, J=9.0Hz), 4.81 (1H, m), 4.94 (1H, m), 5.07 (1H, t, J=9.0Hz), 7.01 (1H, s), 7.73 (1H, s).
SIMS m/z: 395 (M+1)$^+$.

EXAMPLE 4

3-[N$^\alpha$-(trans-3-Methylpyroglutamyl)-L-histidyl]-L-thiazolidine-4-carboxamide (Compound 4)

In the same manner as in Example 3, 3-[N$^\alpha$-(trans-3-methylpyroglutamyl)-L-histidyl]-L-thiazolidine-4-carboxamide (215 mg) was obtained from trans-3-methylpyroglutamic acid (468 mg) and 3-(N$^{im}$-tosyl-L-histidyl)-L-thiazolidine-4-carboxamide hydrochloride (1 g).

NMR (CD$_3$OD): δppm: 1.09–1.23 (3H), 1.91 (1H, dd, J=5.0Hz and 14.0Hz), 2.38 (1H, m), 2.55 (1H, ddd, J=2.0Hz, 7.0Hz and 13.0Hz), 3.02 (1H, m), 3.17 (2H, m), 3.32 (1H), 3.77 (1H, t, J=5.0Hz), 4.40 (1H, dd, J=7.0Hz and 13.0Hz), 4.83–5.05 (3H), 7.00 (1H, s), 7.67 (1H, s).
SIMS m/z: 395 (M+1)$^+$.

EXAMPLE 5

N$^\alpha$-[(2S,3R)-Tetrahydro-3-methyl-5-oxo-2-furancarbonyl]-L-histidyl-L-prolinamide (Compound 5)

Stage A (2S,3R)-Tetrahydro-3-methyl-5-oxo-2-furancarboxylic acid [K. Tomioka et al, *Heterocycles*, 17, 311 (1982)] (144 mg) and pentachlorophenol (266.5 mg) were dissolved in ethyl acetate (10 ml), and DCC (206 mg) was added to the solution under ice-cooling. The mixture was stirred for 2 hours. After the resultant dicyclohexylurea was filtered off, the filtrate was concentrated to dryness to give pentachlorophenol ester (260 mg) in the crystalline form.

Stage B

L-Histidyl-L-prolinamide dihydrobromide (190 mg) was dissolved in DMF (4 ml), whereto triethylamine (0.13 ml) was added under cooling at −10° C. After the mixture was stirred under ice-cooling for 10 minutes, the resultant precipitate was filtered off. To this solution, the above-mentioned pentachlorophenol ester (180 mg) was added under ice-cooling, and the mixture was stirred at 4° C. for 48 hours. The reaction mixture was concentrated under reduced pressure to dryness, and the obtained residue was dissolved in water (1 ml) and washed three times with ether (2 ml). The water layer was subjected to Diaion HP-20 column chromatography (1.0×40 cm) to be washed with water and eluted with a mixture of water-acetone (1:1). The fractions containing the objective compound were combined and concentrated to dryness to give N$^\alpha$-[(2S,3R)-tetrahydro-3-methyl-5-oxo-2 furancarbonyl]-L-histidyl-L-prolinamide (130 mg).

NMR (CD$_3$OD): δppm: 0.89 (3H, d, J=7.0Hz), 1.90–2.03 (3H, m), 2.13–2.32 (2H, m), 2.70 (1H, dd, J=7.0Hz and 8.0Hz), 2.84 (1H, m), 3.03 (1H, dd, J=7.0Hz and 12.0 Hz), 3.13 (1H, dd, J=7.0Hz and 13.0Hz), 3.45 (1H, m), 3.83 (1H, m), 4.39 (1H, dd, J=6.0Hz and 7.0Hz), 4.95 5.04 (2H), 6.96 (1H, s), 7.61 (1H, s).
SIMS m/z: 378 (M+1)$^+$.

EXAMPLE 6

N$^\alpha$-[(2S,4R)-Tetrahydro-4-methyl-5-oxo-2-furancarbonyl]-L-histidyl-L-prolinamide (Compound 6)

In the same method as in Example 5, the title compound (300 mg) was obtained from (2S,4R)-tetrahydro-4-methyl-5-oxo-2-furancarboxylic acid [S. Hanessian et al, *Tetrahedron Lett.*, 26, 5623 (1985)] (432 mg) and L-histidyl-L-prolinamide dihydrobromide (413 mg).

NMR (CD$_3$OD): δppm: 1.20 (3H, d, J=7.0Hz), 1.81–2.07 (3H, m), 2.07–2.35 (2H, m), 2.38–2.81 (2H, m), 3.01 (1H, dd, J=7.0Hz and 13.0Hz), 3.13 (1H, dd, J=7.0Hz and 13.0Hz), 3.42 (1H, m), 3.75 (1H, m), 4.43 (1H, dd, J=6.0Hz and 7.0Hz), 4.85–5.04 (2H), 6.95 (1H, s), 7.63 (1H, s).
SIMS m/z: 378 (M+1)$^+$.

EXAMPLE 7

Nα-(4-Methylpyroglutamyl)-L-histidyl-L-prolinamide
(Compound 7 and Compound 7')

Stage A

To an anhydrous ethanol solution (2 l) containing metal sodium (2.4 g) was added diethyl acetoaminomaloate (135.4 g), and the mixture was stirred for 10 minutes. Thereafter, methyl methacrylate (100 ml) was added. After the mixture was refluxed under heating for 10 hours, it was left cooled. The reaction mixture was neutralized with dilute hydrochloric acid and concentrated under reduced pressure. Water was added to the residue, followed by extraction with ethyl acetate. The ethyl acetate solution was dried and then concentrated to dryness to give 2,2-diethoxycarbonyl-4-methyl-5-oxopyrrolidine (121.5 g).

NMR (CDCl$_3$): δppm: 1.10–1.40 (9H, m), 1.95–2.25 (1H, m), 2.40–2.98 (2H, m), 4.10–4.40 (4H, m).

EIMS m/z: 243 (M$^+$).

Stage B

In ethanol (1.5 l) was dissolved 2,2-diethoxycarbonyl-4-methyl-5-oxopyrrolidine (121.5 g), and thereto was added an aqueous solution (500 ml) containing sodium hydroxide (20 g). The mixture was stirred overnight. After the mixture was neutralized with dilute hydrochloric acid, it was concentrated under reduced pressure. The residue was extracted with ether, and the solvent was distilled off to give the half ester almost free of salt. The oily half ester was subjected to decarboxylation reaction by stirring it under heating at 150° C. for 30 minutes. After cooled, the product was extracted with ethyl acetate. The extract was washed with water, whereafter the solvent was distilled off to give a mixture of the cis- and trans-isomers of 2-ethoxycarbonyl-4-methyl-5-oxopyrrolidine (72 g). The thus-obtained product was recrystallized from ether to afford crystals (37 g) and the mother liquor (29.6 g). The NMR spectra implied that the crystals were the mixture of the cis-stereoisomer and the trans-stereoisomer in the ratio of 2:1, while the mother liquor was the mixture of the cis-stereoisomer and the trans-stereoisomer in the ratio of 1:2. The crystals and the concentrated dry solid of the mother liquor were used in the following reaction.

Stage C

The crystals (2.0 g) of 2-ethoxycarbonyl-4-methyl-5-oxopyrrolidine in the above-mentioned stage B were dissolved in a 2N sodium hydroxide solution (6 ml), and the solution was stirred at room temperature overnight. The mixture was neutralized with dilute hydrochloric acid, followed by concentration under reduced pressure. The residue was crystallized from water to give 4-methylpyroglutamic acid isomer A (900 mg) as crystals.

m.p. 162°–163° C.

NMR (D$_2$O): δppm: 1.10 (3H, d, J=7.3Hz), 2.15 (1H, td, J=9.9Hz and 14.6Hz), 2.42 (1H, ddd, J=3.6Hz, 11.3Hz and 14.6Hz), 2.58 (1H, m), 4.30 (1H, dd, J=3.6Hz and 9.6Hz).

SIMS m/z: 144 (M+1)$^+$.

The concentrated dry solid (2.0 g) of the mother liquor of 2-ethoxycarbonyl-4 methyl-5-oxopyrrolidine in the above-mentioned Stage B was dissolved in a 2N sodium hydroxide solution (6 ml), and the solution was stirred at room temperature overnight, followed by neutralization with dilute hydrochloric acid and concentration under reduced pressure. The residue was crystallized from water to afford 4-methylpyroglutamic acid isomer B (200 mg) as crystals.

m.p. 169°–170° C.

NMR (D$_2$O): δppm: 1.10 (3H, d, J=7.3Hz), 1.74 (1H, td, J=7.9Hz and 13.5Hz), 2.58 (1H, m), 2.74 (1H, td, J=8.2Hz and 13.5Hz), 4.28 (1H, t, J=8.2Hz).

SIMS m/z: 144 (M+1)$^+$.

From the spectral data, it is evident that one of the obtained 4-methylpyroglutamic acid isomers A and B is the single compound of the cis-stereoisomer and the other is the single compound of the trans stereoisomer. These isomers were used in the following synthetic reaction.

Stage D

By the same method as in Example 1, Nα-(4-methylpyroglutamyl)-L-histidyl-L-prolinamide isomer A (420 mg) was obtained from 4-methylpyroglutamic acid isomer A (314 mg) obtained in Stage C and L-histidyl-L-prolinamide 2 hydrobromide (906 mg).

NMR (CD$_3$OD): δppm: 1.12 (3H, d, J=6.1Hz), 1.75–2.07 (4H, m), 2.12–2.35 (2H, m), 2.48 (1H, m), 2.98 (1H, m), 3.12 (1H, dd, J=14.1Hz and 6.6Hz), 3.42 (1H, m), 3.77 (1H, br), 4.11 (1H, m), 4.42 (1H, m), 4.80 (1H, m), 6.90 (0.1H, s), 6.98 (0.9H, s), 7.63 (1H, s).

SIMS m/z: 377 (M+1)$^+$.

By the same method as in Example 1, Nα-(4 methylpyroglutamyl)-L-histidyl-L-prolinamide isomer B (345 mg) was obtained from 4-methylpyroglutamic acid isomer B (303 mg) obtained in Stage C and L-histidyl-L-prolinamide 2 hydrobromide (875 mg).

NMR (CD$_3$OD): δppm: 1.12 (1.5H, d, J=6.1Hz), 1.13 (1.5H, d, J=6.1Hz), 1.58 (1H, m), 1.72–2.07 (3H, m), 2.20 (1H, m), 2.47 (1H, m), 2.62 (1H, m), 2.98 (1H, m), 3.12 (1H, m), 3.40 (1H, m), 3.77 (1H, br), 4.10 (1H, m), 4.41 (1H, m), 4.82 (1H, m), 6.90 (0.1H, s), 7.00 (0.9H, s), 7.69 (1H, s).

SIMS m/z: 377 (M+1)$^+$.

EXAMPLE 8

Nα-(3,3-Dimethylpyroglutamyl)-L-histidyl-L-prolinamide (Compound 8)

By the same method as in Example 1, the title compound (111 mg) was obtained as powders from 3,3-dimethylpyroglutamic acid [T. Yamazaki et al, *Chem. Pharm. Bull.*, 24, 3011 (1976)] (100 mg) and L-histidyl-L-prolinamide dihydrobromide (263 mg).

NMR (CD$_3$OD): δppm: 0.88 (1.5H, s), 0.96 (1.5H, s), 1.20 (1.5H, s), 1.25 (1.5H, s), 1.75–2.10 (4H, m), 2.10–2.35 (2H, m), 2.98 (1H, m), 3.12 (1H, dd, J=14.0Hz and 7.0Hz), 3.44 (1H, m), 3.77 (0.5H, s), 3.80 (0.5H, s), 3.86 (1H, m), 4.41 (1H, dd, J=8.3Hz and 4.1Hz), 4.87 (1H, m), 6.96 (0.5H, s), 6.98 (0.5H, s), 7.62 (1H, s).

EXAMPLE 9

3-[Nα-(3,3-Dimethylpyroglutamyl)-L-histidyl]-L-thiazolidine-4-carboxamide (Compound 9)

By the same method as in Example 3, the title compound (117 mg) was obtained as powders from 3,3-dimethylpyroglutamic acid [T. Yamazaki et al, *Chem. Pharm. Bull.*, 24, 3011 (1976)] (100 mg) and 3-(N$^{im}$-tosyl-L-histidyl)-L-thiazolidine-4-carboxamide hydrochloride (615 mg).

NMR (CD$_3$OD): δppm: 0.89 (1.5H, s), 0.97 (1.5H, s), 1.20 (1.5H, s), 1.24 (1.5H, s), 2.01 (0.5H, d, J=16.4Hz), 2.03 (0.5H, d, J=16.5Hz), 2.28 (0.5H, d, J=16.5Hz), 2.29 (0.5H, d, J=16.5Hz), 3.01 (1H, m), 3.10-3.35 (3H, m), 3.77 (0.5H, s), 3.79 (0.5H, s), 4.43 (0.5H, d, J=9.0Hz), 4.46 (0.5H, d, J=9.3Hz), 4.82 (1H, m), 4.95 (1H, m), 5.06 (0.5H, d, J=8.5Hz), 5.08 (0.5H, d, J=8.6Hz), 7.02 (1H, s), 7.72 (1H, s).

EXAMPLE 10

N$^α$-(trans-3-Phenylpyroglutamyl) L-histidyl-L-prolinamide (Compound 10)

By the same method as in Example 1, the title compound (210 mg) was obtained as powders from trans-3-phenylpyroglutamic acid [F. Zymalkowski, P. Pachaly, *Chem. Ber.*, 100, 1137 (1967)] (180 mg) and L-histidyl-L-prolinamide dihydrobromide (363 mg).

NMR (CD$_3$OD): δppm: 1.70-2.05 (3H, m), 2.05-2.30 (1H, m), 2.41 (1H, m), 2.70-3.15 (3H, m), 3.35-3.65 (2H, m), 3.76 (1H, m), 4.17 (1H, m), 4.41 (1H, m), 4.83 (1H, m), 6.86 (0.5H, s), 6.97 (0.5H, s), 7.10-7.40 (5H, m), 7.65 (1H, s).

EXAMPLE 11

N$^α$-(cis-3-Phenylpyroglutamyl)-L-histidyl-L-prolinamide (Compound 11)

By the same method as in Example 1, the title compound (103 mg) was obtained as powders from cis-3-phenylpyroglutamic acid [F. Zymalkowski, P. Pachaly, *Chem. Ber.*, 100, 1137 (1967)] (140 mg) and L-histidyl-L-prolinamide dihydrobromide (330 mg).

NMR (CD$_3$OD): δppm: 1.65-2.05 (3H, m), 2.16 (1H, m), 2.50-3.00 (3H, m), 3.10 (1H, m), 3.25-3.65 (1H, m), 4.02 (1H, m), 4.15-4.60 (3H, m), 6.69 (0.5H, s), 6.90 (0.5H, s), 7.10-7.40 (5H, m), 7.63 (0.5H, s), 7.68 (0.5H, s).

EXAMPLE 12

N$^α$-(3-Oxocyclobutanecarbonyl)-L-histidyl-L-prolinamide (Compound 12)

By the same method as in Example 1, the title compound (184 mg) was obtained from 3-oxocyclobutanecarboxylic acid [P. E. Pigou and C. H. Schiesser, *J. Org. Chem.*, 53, 3841 (1988)] (184 mg) and L-histidyl-L-prolinamide dihydrobromide (668 mg).

NMR (CD$_3$OD): δppm: 1.72-2.33 (4H, m), 2.98 (1H, dd, J=7Hz and 13Hz), 3.11 (1H, dd, J=7Hz and 14Hz), 3.16-3.31 (5H, m), 3.37-3.49 (1H, m), 3.72-3.87 (1H, m), 4.40-4.51 (1H, m), 4.85 (1H, t, J=7Hz), 6.98 (1H, s), 7.67 (1H, s).

CIMS m/z: 348 (M+1)$^+$.

EXAMPLE 13

N$^α$-(3-Oxocyclopentanecarbonyl)-L-histidyl-L-prolinamide (Compound 13)

By the same method as in Example 1, the title compound (222 mg) was obtained as powders from 3-oxocyclopentanecarboxylic acid [K. Curry, M. J. Peet, D. S. K. Magunuson and H. McLennan, *J. Med. Chem.*, 31, 864 (1988)] (158 mg) and L-histidyl-L-prolinamide dihydrobromide (510 mg).

NMR (CD$_3$OD): δppm: 1.73-2.11 (4H, m), 2.11-2.38 (6H, m), 2.97 (1H, dd, J=7Hz and 14Hz), 3.11 (2H, dd, J=7Hz and 14Hz), 3.30-3.41 (1H, m), 3.72-3.83 (1H, m), 4.43 (1H, dd, J=4Hz and 9Hz), 4.81 (1H, t, J=7Hz), 6.96 (1H, s), 7.62 (1H, s).

CIMS m/z: 362 (M+1)$^+$.

EXAMPLE 14

N$^α$-(3-Oxocyclohexanecarbonyl)-L-histidyl-L-prolinamide (Compound 14)

By the same method as in Example 1, the title compound (103 mg) was obtained as powders from 3-oxocyclohexanecarboxylic acid [R. D. Allan, G. A. R. Johnston and B. Twitchin, *Aust. J. Chem.*, 34, 2231 (1981)] (172 mg) and L-histidyl-L-prolinamide dihydrobromide (500 mg).

NMR (CD$_3$OD): δppm: 1.25-2.09 (8H, m), 2.16-2.42 (3H, m), 2.42-2.57 (1H, m), 2.71-2.82 (1H, m), 2.94 (1H, dd, J=7Hz and 14Hz), 3.07 (1H, dd, J=7Hz and 14Hz), 3.78 (1H, q, J=8Hz), 4.40-4.48 (1H, m), 4.72-4.85 (1H, m), 4.91-5.02 (1H, m), 6.98 (1H, s), 7.66 (1H, s).

CIMS m/z: 376 (M+1)$^+$.

EXAMPLE 15

3-[N$^α$-(3-Oxocyclohexanecarbonyl)-L-histidyl]-L-thiazolidine-4-carboxyamide (Compound 15)

By the same method as in Example 3, the title compound (208 mg) was obtained from 3-oxocyclohexanecarboxylic acid (231 mg) and 3-(N$^{im}$-tosyl-L-histidyl)-L-thiazolidine-4-carboxamide (I. Soboe et al, Japanese Patent Unexamined Publication No. 190795/1985] (500 mg).

NMR (CD$_3$OD): δppm: 1.22-1.57 (1H, m), 1.57 2.11 (4H, m), 2.12-2.42 (2H, m), 2.42-2.55 (1H, m), 2.70-2.82 (1H, m), 2.91-3.02 (1H, m), 3.04-3.22 (2H, m), 3.27-3.36 (1H, m), 4.36 (1H, dd, J=7Hz and 8Hz), 4.61-4.78 (1H, m), 4.80-4.91 (1H, m), 4.91 4.99 (1H, m), 6.94 (1H, s), 7.60 (1H, s).

CIMS m/z: 394 (M+1)$^+$.

EXAMPLE 16

N$^α$-[(1R)-3-Oxocyclopentanecarbonyl]-L-histidyl-L-prolinamide (Compound 16)

By the same method as in Example 1, the title compound (222 mg) was obtained as powders from (1R) 3-oxocyclopentane-carboxylic acid [K. Toki et al, *Bull. Chem. Soc. Jpn.*, 31, 333 (1958)] (158 mg) and L-histidyl-L-prolinamide dihydrobromide (510 mg).

NMR (CD$_3$OD): δppm: 1.70-2.40 (10H, m), 2.96 (1H, dd, J=14.6Hz and 6.7Hz), 3.00-3.15 (2H, m), 3.33 (1H, m), 3.77 (1H, m), 4.43 (1H, dd, J=8.3Hz and 4.2Hz), 4.78 (1H, t, J=7.0Hz), 6.95 (1H, s), 7.62 (1H, s).

EXAMPLE 17

3-[N$^α$-(3-Oxocyclopentanecarbonyl)-L-histidyl]-L-thiazolidine-4-carboxyamide (Compound 17)

By the same method as in Example 3, the title compound (137 mg) was obtained as powders from 3-(N$^{im}$-tosyl-L-histidyl)-L-thiazolidine-4-carboxyamide hydrochloride (400 mg) and 3-oxocyclopentanecarboxylic acid (168 mg).

NMR (CD$_3$OD): δppm: 1.83-2.42 (6H, m), 2.92-3.23 (5H, m), 4.37 (1H, t), 4.61 5.10 (3H, m), 6.98 (1H, s), 7.64 (1H, s).

CIMS m/z: 380 (M.1)$^+$.

EXAMPLE 18

N$^α$-[(1R)-3-Oxocyclopentanecarbonyl]-L-histidyl 3,3-dimethylprolinamide (Compound 18)

By the same method as in Example 1, the title compound (214 mg) was obtained as powders from (1R)-3- oxocyclopentanecarboxylic acid [K. Toki et al, *Bull. Chem. Soc. Jpn.*, 31, 333 (1958)] (120 mg) and L-histidyl-3,3-dimethylprolinamide 2 dihydrobromide [Ger. Offen. 2609154 (1976) and Japanese Patent Unexamined Publication No. 116465/1977 (1977)] (413 mg).

NMR (CD$_3$OD): δppm: 0.88 (1.5H, s), 1.04 (1.5H, s), 1.10 (1.5H, s), 1.17 (1 5H, s), 1.58 (0.5H, m), 1.73 (0.5H, m), 1.80–2.10 (2H, m), 2.10–2.40 (5H, m), 2.85–3.15 (3H, m), 3.22 (0.5H, m), 3.48 (0.5H, m), 3.78 (0.5H, s), 3.84 (0.5H, m), 3.97 (0.5H, m), 4.02 (0.5H, s), 4.77 (1H, s), 6.88 (0.5H, s), 6.92 (0.5H, s), 7.61 (0.5H, s), 7.64 (0.5H, s).

EXAMPLE 19

N$^α$-(cis-2-Methyl-4-oxocyclopentanecarbonyl)-L-histidyl-L-prolinamide (Compound 19)

By the same method as in Example 1, the title compound (306 mg) was obtained from cis-2-methyl-4 oxocyclopentanecarboxylic acid (213 mg) and L-histidyl-L-prolinamide dihydrobromide acid (620 mg).

NMR (CD$_3$OD): δppm: 0.86 (1.5H, d, J=7.0Hz), 1.01 (1.5H, d, J=7.0Hz), 1.70–2.15 (5H, m), 2.15–2.50 (4H, m), 2.60 (1H, m), 2.98 (1H, dd, J=14.0Hz and 6.9Hz), 3.08 (1H, m), 3.33–3.50 (1H, m), 3.83 (1H, m), 4.44 (1H, m), 4.83 (1H, m), 6.97 (0.5H, s), 7.00 (0.5H, s), 7.61 (1H, s).

CIMS m/z: 376 (M+1)$^+$.

EXAMPLE 20

N$^α$-(trans-2-Methyl-4-oxocyclopentanecarbonyl)-L-histidyl-L-prolinamide (Compound 20)

By the same method as in Example 1, the title compound (150 mg) was obtained from trans-2-methyl 4 oxocyclopentanecarboxylic acid (190 mg) and L-histidyl-L-prolinamide dihydrobromide (552 mg).

NMR (CD$_3$OD): δppm: 1.02 (1.5H, d, J=7.0Hz), 1.13 (1.5H, d, J=7.0Hz), 1.70–2.10 (4H, m), 2.10 2.60 (5H, m), 2.67 (1H, m), 3.00 (1H, m), 3.15 (1H, m), 3.45 (1H, m), 3.89 (1H, m), 4.47 (1H, m), 4.85 (1H, m), 6.98 (0.5H, s), 7.02 (0.5H, s), 7.65 (1H, s).

CIMS m/z: 376 (M+1)$^+$.

EXAMPLE 21

N$^α$-(2,2-Dimethyl-4-oxocyclopentanecarbonyl)-L-histidyl-L-prolinamide (Compound 21)

In DMF (2 ml) was dissolved 2,2 dimethyl-4-oxocyclopentanecarboxylic acid [W. H. Perkin, jun., J. F. Thorpe, *J. Chem. Soc.*, 79, 729 (1901)] (100 mg), and HOBT (108 mg) was added to the solution, followed by addition of DCC (145 mg) under cooling at 0° C. The mixture was stirred at 5° C. over night. After addition of L-histidyl-L-prolinamide dihydrobromide (265 mg) followed by addition of triethylamine (0.134 ml), the mixture was stirred at 5° C. for 4 days. After the resultant precipitate was filtered off, the filtrate was concentrated under reduced pressure to dryness and the residue was subjected to silica gel column chromatography. The fractions eluted by chloroform:methanol:ammonia water (90:10:2) were combined and concentrated to dryness to give the title compound (140 mg) was obtained as powders.

NMR (CD$_3$OD): δppm: 0.88 (1.5H, s), 1.00 (1.5H, s), 1.10 (1.5H, s), 1.21 (1.5H, s), 1.65–2.30 (6H, m), 2.44 (2H, m), 2.82 (1H, m), 2.96 (1H, m), 3.10 (1H, dd, J=15.0Hz and 7.2Hz), 3.30–3.55 (1H, m), 3.82 (1H, m), 4.43 (1H, m), 4.83 (1H, m), 6.94 (0.5H, s), 6.98 (0.5H, s), 7.60 (0.5H, s), 7.61 (0.5H, s).

EXAMPLE 22

N$^α$-(3-Oxospiro[4.5]decane-1-carbonyl)-L-histidyl-L-prolinamide (Compound 22)

By the same method as in Example 1, the title compound (220 mg) was obtained from 1-carboxy-3-oxospiro[4.5]decane (150 mg) and L-histidyl-L-prolinamide dihydrobromide (389 mg).

NMR (CD$_3$OD): δppm: 1.09–1.71 (10H, m), 1.85–2.52 (8H, m), 2.72–3.01 (2H, m), 3.10 (1H, dd), 3.42–3.56 (1H, m), 3.74–3.92 (1H, m), 4.31–4.46 (1H, m), 6.93 (0.5H, s), 6.98 (0.5H, s), 7.60 (0.5H, s), 7.62 (0.5H, s).

SIMS m/z: 431 (M.2)$^+$.

EXAMPLE 23

3-[N$^α$-(2-Aza-3-oxospiro[4.5]decane-1-carbonyl)-L-histidyl]-L-thiazolidine-4-carboxamide (Compound 23)

By the same method as in Example 3, the title compound (10 mg) was obtained from 2-aza-1-carboxy-3-oxospiro[4.5]-decane (47 mg) and 3-(N$^{im}$-tosyl-L-histidyl)-L-thiazolidine-4-carboxamide hydrochloride (167 mg).

NMR (CD$_3$OD): δppm: 1.00–1.70 (10H, m), 2.16 (0.5H, d, J=16.5Hz), 2.18 (0.5H, d, J=16.5Hz), 2.28 (0.5H, d, J=16.5Hz), 2.29 (0.5H, d, J=16.5Hz), 3.00 (1H, m), 3.08–3.20 (2H, m), 3.20–3.40 (1H, m), 3.76 (0.5H, s), 3.79 (0.5H, s), 4.46 (0.5H, d, J=8.7Hz), 4.52 (0.5H, d, J=8.7Hz), 4.70–5.00 (2H, m), 5.08 (0.5H, d, J=8.7Hz), 5.10 (0.5H, d, J=8.7Hz), 7.03 (0.5H, s), 7.05 (0.5H, s), 7.78 (0.5H, s), 7.79 (0.5H, s).

EXAMPLE 24

3[N$^α$-(cis-3-Ethylpyroglutamyl)-L-histidyl]-L-thiazolidine-4-carboxamide (Compound 24)

According to the method of G. H. Cocolas et al [G. H. Cocolas et al, *J. Am. Chem. Soc.*, 79, 5203 (1957)], 21.2 g of 5,5-dicarboethoxy-4-ethyl-2-pyrrolidinone was obtained from ethyl 2-pentenate (16.5 g) and diethyl acetamidomalonate (18.7 g). From 5,5-dicarboethoxy-4-ethyl-2-pyrrolidinone (20 g), the mixture (13.2 g) of ethyl cis-3-ethylpyroglutamate and ethyl trans-3-ethylpyroglutamate was obtained in the ratio of 1:1 according to the method of A. B. Mauger [A. B. Mauger, *J. Org. Chem.*, 46, 1032 (1981)]. The obtained mixture was subjected to silica gel column chromatography (ethyl acetate) to afford 1.85 g of a mixture whose primary component was cis-isomer. The mixture thus obtained was hydrolyzed by the method of A. B. Mauger to afford 785 mg of the mixture of cis-3-ethylpyroglutamic acid and trans-3-ethylpyroglutamic acid in the ratio of 4.7:1. From this mixture (200 mg) and 3-(N$^{im}$-tosyl-L-histidyl)-L-thiazolidine-4-carboxamide hydrochrolide (874 mg), the title compound (180 mg) was obtained as powders by the same method as in Example 1.

NMR (CD$_3$OD): δppm: 0.84–0.93 (3H, m), 0.98–1.08 (1H, m), 1.08 1.34 (0.5H, m), 1.41 1.65 (0.5H, m), 2.08 (1H, m), 2.31 (1H, m), 2.40–2.63 (1H, m), 2.88–3.05 (1H, m), 3.04–3.22 (2H, m), 4.14 (1H, t, J=8.2Hz), 4.45 (1H, dd, J=16.4Hz and 9.0Hz), 4.78–4.86 (1H, m), 5.07 (1H, t, J=9.0Hz), 6.98 (0.5H, s), 6.99 (0.5H, s), 7.65 (0.5H, s), 7.66 (0.5H, s).

SIMS m/z: 409 (M+1)$^+$.

EXAMPLE 25

N$^\alpha$-(cis-3-Methylpyroglutamyl)-L-histidyl-3,3-dimethylprolinamide (Compound 25)

By the same method as in Example 21, the title compound (277 mg) was obtained as powders from cis-3-methylpyroglutamic acid (150 mg) and L-histidyl-3,3-dimethylprolinamide dihydrobromide(508 mg).

NMR (CD$_3$OD): δppm: 0.76–1.20 (9H, m), 1.50–1.68 (0.5H, m), 1.68–1.82 (0.5H, m), 1.82–2.14 (2H, m), 2.24–2.42 (1H, m), 2.62–2.88 (1H, m), 2.88–3.18 (2H, m), 3.46–3.72 (1H, m), 3.84–4.06 (1H,m), 4.02 (1H, s), 4.06–4.22 (1H, m), 6.96 (1H, bs), 7.72 (1H, bs).

SIMS m/z: 404(M+1)$^+$.

EXAMPLE 26

N$^\alpha$-(cis-2-Ethyl-4-oxocyclopentanecarbonyl)-L-histidyl-L-prolinamide (Compound 26)

In the same manner as in Example 1, N$^\alpha$-(cis-2-ethyl-4-oxocyclopentanecarbonyl)-L-histidyl-L-prolinamide (2.77 g) was obtained from cis-2-ethyl-4-oxocyclopentanecarboxylic acid (2.50 g) and L-histidyl-L-prolinamide 2 hydrobromide (6.62 g).

The compound obtained above is a mixture of two diastereomers which could be separated by HPLC to give the less polar compound (26A) and the more polar compound (26B).

Compound 26A.

NMR (CD$_3$OD): δppm: 0.94 (3H, t, J=7.4Hz), 1.15–1.45 (1H, m), 1.45–1.66 (1H, m), 1.70–2.50 (9H, m), 2.90–3.05 (1H, m), 3.05–3.20 (2H, m), 3.30 3.40 (1H, m), 3.75–3.90 (1H, m) 4.40–4.50 (1H, m), 4.75–4.90 (1H, m), 6.93 (1H, s), 7.59 (1H, s).

CIMS m/z: 390(M+1)$^+$.

Compound 26B. δppm: 0.86 (3H, t, J=7.4Hz), 1.00–1.15 (1H, m), 1.15–1.42 (1H, m), 1.70–2.50 (9H, m), 2.90–3.05 (1H, m), 3.05–3.20 (2H, m), 3.45–3.55 (1H, m), 3.75–3.90 (1H, m) 4.40–4.50 (1H, m), 4.75–4.90 (1H, m), 6.97 (1H, s), 7.61 (1H, s).

CIMS m/z: 390(M+1)$^+$.

EXAMPLE 27

N-(cis-3-Methylpyroglutamyl)-L-leucyl-L-prolinamide (Compound 27A and 27B)

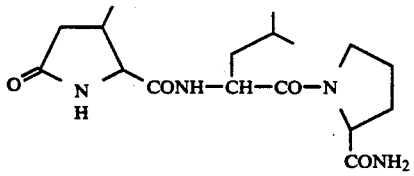

L-Leucyl-L-prolinamide hydrobromide (517 mg) was dissolved in DMF (1.5 ml), to which was added triethylamine (0.35 ml) under cooling at −10° C. The mixture was stirred for 10 minutes under ice-cooling and the resultant precipitate was filtered off to give L-leucyl-L-prolinamide in DMF solution, which was immediately used for the next reaction.

cis-3-Methylpyroglutamic acid [A. B. Mauger, *J. Org. Chem.*, 46, 1032 (1981)] (200 mg) was dissolved in DMF (1.5 ml), to which was added HOBT (257 mg), followed by cooling to 0° C. DCC (317 mg) was added thereto and the mixture was stirred at 0° C. overnight. To the mixture was added the above-mentioned L-leucyl-L-prolinamide in DMF, and the mixture was stirred at 5° C. overnight. The resultant precipitate was filtered off and concentrated to dryness under reduced pressure. The residue was washed with water and purified by HP-20 column chromatography (1.0×40cm) with methanol as eluent. The eluted fraction was concentrated to dryness under reduced pressure, and the residue obtained was purified by silica gel column chromatography (developing solvent: chloroform:methanol:ammonia water=60:10:1) to give the title less polar compound 27A (188 mg) and the more polar compound 27B (177 mg) as powders. The compounds 27A and 27B have diastereomeric relationship to each other.

Compound 27A.

NMR (CD$_3$OD): δppm: 0.90–1.10 (9H, m), 1.55–1.82 (3H, m), 1.89–2.29 (5H, m), 2.35–2.44 (1H, m), 2.72–2.88 (1H, m), 3.61–3.71 (1H, m), 3.86–3.98 (1H, m), 4.19 (1H, d), 4.35–4.45 (1H, m), 4.59–4.68 (1H, m).

CIMS m/z: 353(M+1)$^+$.

Compound 27B.

NMR (CD$_3$OD): δppm: 0.90–1.10 (9H, m), 1.55–1.84 (3H, m), 1.55–1.84 (3H, m), 1.85 2.29 (5H, m), 2.30–2.44 (1H, m), 2.72–2.90 (1H, m), 3.61–3.72 (1H, m), 3.85–3.95 (1H, m), 4.15 (1H, d), 4.43 4.53 (1H, m), 4.60–4.69 (1H, m).

EXAMPLE 28

N-(cis-3-Methylpyroglutamyl)-L-methionyl-L-prolinamide (Compound 28A and 28B)

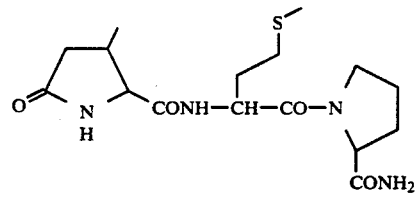

In the same manner as in Example 27, the title less polar compound 28A (140 mg) and the more polar compound 28B (150 mg) were obtained each as a powder from L-methionyl-L-prolinamide hydrobromide (685 mg) and cis-3-methylpyroglutamic acid (300 mg). The compounds 28A and 28B have distereomeric relationship to each other.

Compound 28A.

NMR (CD$_3$OD): δppm: 1.00 (3H, d, J=7.0Hz), 1.86–2.30 (10H, m), 2.39 (1H, d, J=8.5Hz and 16.5Hz), 2.51–2.72 (2H, m), 2.73–2.88 (1H, m), 3.69–3.80 (1H, m), 3.90–3.99 (1H, m), 4.18 (1H, d, J=8.0Hz), 4.40 (1H, dd, J=4.8Hz and 8.3Hz).

CIMS m/z: 371(M+1)$^+$.

Compound 28B.

NMR (CD$_3$OD): δppm: 1.05 (3H, d, J=7.0Hz), 1.86–2.26 (10H, m), 2.37 (1H, d, J=8.5Hz and 16.5Hz), 2.52–2.72 (2H, m), 2.73 2.86 (1H, m), 3.68–3.70 (1H, m), 3.86–3.96 (1H, m), 4.15 (1H, d, J=8.1Hz), 4.41 (1H, dd, J=4.8Hz and 8.2Hz), 4.82 (1H, dd, J=5.2Hz and 8.9Hz).

EXAMPLE 29

N-(cis-3-Methylpyroglutamyl)-L-norvalyl-L-prolinamide (Compound 29A and 29B)

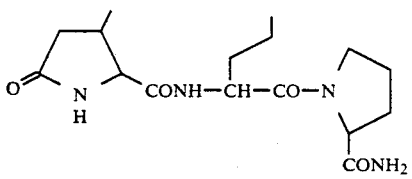

In the same manner as in Example 27, the title less polar compound 29A (250 mg) and the more polar compound 29B (241 mg) were obtained each as a powder from L-norvalyl-L-prolinamide hydrobromide (618 mg) and cis-3-methylpyroglutamic acid (300 mg). The compounds 29A and 29B have diastereomeric relationship to each other.

Compound 29A.

NMR (CD$_3$OD): δppm: 0.89–1.10 (6H, m), 1.35–1.55 (2H, m), 1.55–1.74 (1H, m), 1.74–2.29 (6H, m), 2.38 (1H, dd, J=8.5Hz and 16.4Hz), 2.71–2.88 (1H, m), 3.60–3.72 (1H, m), 3.85–3.97 (1H, m), 4.19 (1H, d, J=8.0Hz), 4.39 (1H, dd, J=4.7Hz and 8.2Hz), 4.64 (1H, dd, J=5.2Hz and 8.9Hz).

CIMS m/z: 339(M+1)$^+$.

Compound 29B

NMR (CD$_3$OD): δppm: 0.97 (3H, t, J=7.3Hz), 1.05 (3H, d, J=7.0Hz), 1.35–1.60 (2H, m), 1.60–1.73 (1H, m), 1.73–2.30 (6H, m), 2.35 (1H, dd, J=8.5Hz and 16.5Hz), 2.71–2.86 (1H, m), 3.61–3.72 (1H, m), 3.82–3.93 (1H, m), 4.16 (1H, d, J=8.1Hz), 4.39 (1H, dd, J=4.7Hz and 8.2Hz), 4.57 (1H, dd, J=4.9Hz and 9.1Hz).

EXAMPLE 30

N-(cis-3-Methylpyroglutamyl)-L-phenylalanyl-L-prolinamide (Compound 30A and 30B)

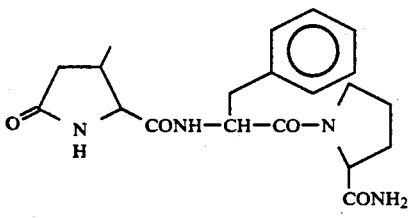

In the same manner as in Example 27, the title less polar compound 30A (250 mg) and the more polar compound 30B (150 mg) were obtained each as a powder from L-phenylalanyl-L-prolinamide hydrobromide (719 mg) and cis-3-methylpyroglutamic acid (300 mg). The compounds 30A and 30B have diastereomeric relationship to each other.

Compound 30A.

NMR (CD$_3$OD): δppm: 0.84 (2.4H, d, J=7.0Hz), 1.01 (0.6H, d, J=7.0Hz), 1.61–2.25 (5H, m), 2.33 (1H, dd, J=8.5Hz and 16.6Hz), 2.67–2.82 (1H, m), 2.86–3.20 (1H, m), 3.15–3.25 (1H, m), 3.47–3.68 (1H, m), 3.88–3.99 (1H, m), 4.11 (0.8H, d, J=8.1Hz), 4.15 (0.2H, d, J=8.0Hz), 4.35–4.46 (1H, m), 7.15 7.42 (5H, m).

CIMS m/z: 387(M+1)$^+$.

Compound 30B

NMR (CD$_3$OD): δppm: 0.57 (2.4H, d, J=7.0Hz), 0.94 (0.6H, d, J=7.0Hz), 1.62–2.41 (6H, m), 2.55–2.72 (1H, m), 2.81–3.03 (1H, m), 3.16–3.28 (1H, m), 3.58–3.77 (1H, m), 3.85–3.97 (1H, m), 4.08 (0.8H, d, J=8.0Hz), 4.16 (0.2H, d, J=8.0Hz), 4.35–4.45 (1H, m), 7.15–7.45 (5H, m).

EXAMPLE 31

N-(cis-3-Methylpyroglutamyl)-L-norleucyl-L-prolinamide (Compound 31A and 31B)

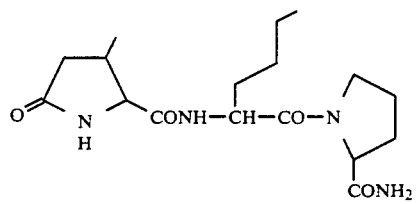

In the same manner as in Example 27, the title less polar compound 31A (220 mg) and the more polar compound 31B (160 mg) were obtained each as a powder from L-norleucyl-L-prolinamide hydrobromide (647 mg) and cis-3-methylpyroglutamic acid (300 mg). The compounds 31A and 31B have diastereomeric relationship to each other.

Compound 31A.

NMR (CD$_3$OD): δppm: 0.82–1.13 (6H, m), 1.25–1.55 (4H, m), 1.58–1.77 (1H, m), 1.77–2.31 (6H, m), 2.38 (1H, dd, J=8.5Hz and 16.5Hz), 2.70–2.90 (1H, m), 3.57–3.72 (1H, m), 3.83–3.99 (1H, m), 4.19 (1H, d, J=8.0Hz), 4.39 (1H, dd, J=4.7Hz and 8.2Hz), 4.62 (1H, dd, J=5.1Hz and 9.0Hz).

CIMS m/z: 353(M+1)$^+$.

Compound 31B.

NMR (CD$_3$OD): δppm: 0.94 (3H, t, J=6.9Hz and 7.1Hz), 1.05 (3H, d, J=7.0Hz), 1.29 1.55 (4H, m), 1.55–1.76 (1H, m), 1.76–2.31 (6H, m), 2.35 (1H, dd, J=8.5Hz and 16.5Hz), 2.69–2.89 (1H, m), 3.57–3.74 (1H, m), 3.80–3.96 (1H, m), 4.16 (1H, d, J=8.1Hz), 4.39 (1H, dd, J=4.7Hz and 8.2Hz), 4.56 (1H, dd, J=4.9Hz and 9.2Hz).

EXAMPLE 32

N-(3,3-Dimethylpyroglutamyl)-L-leucyl-L-prolinamide (Compound 32A and 32B)

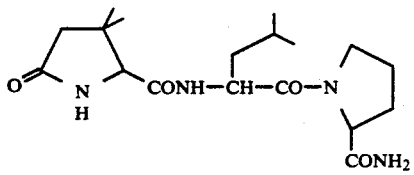

In the same manner as in Example 27, the title less polar compound 32A (85 mg) and the more polar compound 32B (63 mg) were obtained each as a powder from L-leucyl-L-prolinamide hydrobromide (432 mg) and 3,3-dimethylpyroglutamic acid [T. Yamazaki et al, Chem. Pharm. Bull., 24, 3011 (1976)] (200 mg). The compounds 32A and 32B have diastereomeric relationship to each other.

Compound 32A.

NMR (CD$_3$OD): δppm: 0.96 (3H, d, J=6.0Hz), 0.98 (3H, d, J=6.0Hz), 1.02 (3H, s), 1.26 (3H, s), 1.60–1.70 (2H, m), 1.70–1.80 (1H, m), 1.90–2.30 (4H, m), 2.04 (1H, d, J=16.5Hz), 2.30 (1H, d, J=16.5Hz), 3.60–3.70 (1H, m), 3.83 (1H, s), 3.87–3.98 (1H, m), 4.39 (1H, dd, J=8.0Hz and 4.5Hz), 4.72 (1H, dd, J=9.0Hz and 5.0Hz).

CIMS m/z: 367(M+1)+.

Compound 32B.

NMR (CD$_3$OD): δppm: 0.96 (3H, d, J=6.5Hz), 0.99 (3H, d, J=6.5Hz), 1.08 (3H, s), 1.26 (3H, s), 1.55–1.70 (2H, m), 1.70–1.85 (1H, m), 1.85–2.30 (4H, m), 2.02 (1H, d, J=16.5Hz), 2.36 (1H, d, J=16.5Hz), 3.60–3.70 (1H, m), 3.80 (1H, s), 3.83–3.95 (1H, m), 4.39 (1H, dd, J=8.0Hz), 4.63 (1H, dd, J=10.0Hz and 4.5Hz).

EXAMPLE 33

N-(3,3-Dimethylpyroglutamyl)-L-norvalyl-L-prolinamide (Compound 33A and 33B)

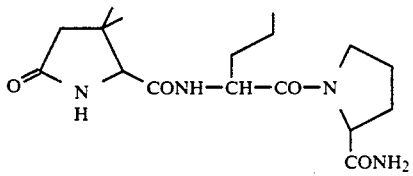

In the same manner as in Example 27, the title less polar compound 33A (215 mg) and the more polar compound 33B (175 mg) were obtained each as a powder from L-norvalyl-L-prolinamide hydrobromide (702 mg) and 3,3-dimethylpyroglutamic acid (250 mg). The compounds 33A and 33B have diastereomeric relationship to each other.

Compound 33A. NMR (CD$_3$OR): δppm: 0.96 (3H, t, J=7.0Hz), 1.02 (3H, s), 1.25 (3H, s), 1.35–1.55 (2H, m), 1.55–1.75 (1H, m), 1.75–1.90 (1H, m), 1.90–2.30 (4H, m), 2.04 (1H, d, J=16.5Hz), 2.30 (1H, d, J=16.5Hz), 3.60–3.70 (1H, m), 3.83–3.95 (1H, m), 4.40 (1H, dd, J=8.0Hz), 4.64 (1H, dd, J=8.0Hz and 4.0Hz).

CIMS m/z: 353(M+1)+.

Compound 33B.

NMR (CD$_3$OD): δppm: 0.97 (3H, t, J=7.0Hz), 1.08 (3H, s), 1.26 (3H, s), 1.40–1.60 (2H, m), 1.60–1.75 (1H, m), 1.75–1.90 (1H, m), 1.90–2.30 (4H, m), 2.02 (1H, d, J=16.5Hz), 2.35 (1H, d, J=16.5Hz), 3.60–3.70 (1H, m), 3.80 (1H, s), 4.41 (1H, dd, J=7.5Hz and 4.0Hz), 4.57 (1H, dd, J=8.0Hz and 4.0Hz).

EXAMPLE 34

N-(3,3-Dimethylpyroglutamyl)-L-methionyl-L-prolinamide (Compound 34A and 34B)

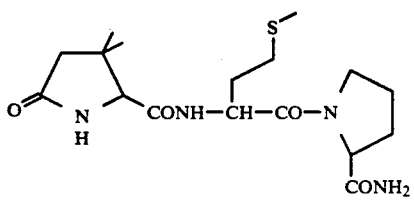

In the same manner as in Example 27, the title less polar compound 34A (212 mg) and the more polar compound 34B (195 mg) were obtained each as a powder from L-methionyl-L-prolinamide hydrobromide (778 mg) and 3,3-dimethylpyroglutamic acid (250 mg). The compounds 34A and 34B have diastereomeric relationship to each other.

Compound 34A.

NMR (CD$_3$OD): δppm: 1.03 (3H, s), 1.26 (3H, s), 1.85–2.30 (6H, m), 2.04 (1H, d, J=16.5Hz), 2.11 (3H, s), 2.30 (1H, d, J=16.5Hz), 2.50–2.70 (2H, m), 3.70–3.80 (1H, m), 3.82 (1H, s), 3.90–4.00 (1H, m), 4.39 (1H, dd, J=8.0Hz and 4.5Hz).

CIMS m/z: 385(M+1)+.

Compound 34B.

NMR (CD$_3$OD): δppm: 1.08 (3H, s), 1.26 (3H, s), 1.85–2.30 (6H, m), 2.02 (1H, d, J=16.5Hz), 2.11 (3H, s), 2.36 (1H, d, J=16.5Hz), 2.55–2.75 (2H, m), 3.70–3.80 (1H, m), 3.79 (1H, s), 3.90–4.00 (1H, m), 4.40 (1H, dd, J=8.0Hz and 4.5Hz), 4.81 (1H, dd, J=9.0Hz and 5.0Hz).

EXAMPLE 35

N-(3,3-Dimethylpyroglutamyl)-L-phenylalanyl-L-prolinamide (Compound 35A and 35B)

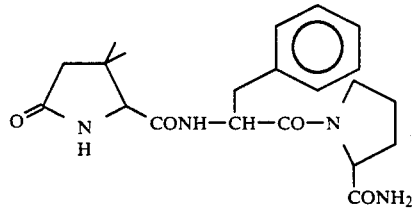

In the same manner as in Example 27, the title less polar compound 35A (206 mg) and the more polar compound 35B (140 mg) were obtained each as a powder from L-phenylalanyl-L-prolinamide hydrobromide (654 mg) and 3,3-dimethylpyroglutamic acid (300 mg). The compounds 35A and 35B have diastereomeric relationship to each other.

Compound 35A.

NMR (CD$_3$OD): δppm: 0.85 (2.3H, s), 1.04 (0.7H, s), 1.21 (2.3H, s), 1.25 (0.7H, s), 1.64–2.13 (4H, m), 2.13–2.40 (2H, m), 2.91–3.15 (1H, m), 3.18–3.32 (1H, m), 3.51–3.72 (1H, m), 3.74 (0.8H, s), 3.84 (0.2H, s), 3.90–4.02 (1H, m), 4.38–4.50 (1H, m), 7.20–7.42 (5H, m).

CIMS m/z: 401(M+1)+.

Compound 35B.

NMR (CD$_3$OD): δppm: 0.61 (2.4H, s), 0.97 (0.6H, s), 1.12 (2.4H, s), 1.23 (0.6H, s), 1.67–2.14 (4H, m), 2.14–2.42 (2H, m), 2.84–3.09 (1H, m), 3.21–3.32 (1H, m), 3.61–3.72 (1H, m), 3.73 (0.8H, s), 3.80 (0.2H, s), 3.91–4.02 (1H, m), 4.38 4.50 (1H, m), 7.19–7.43 (5H, m).

EXAMPLE 36

N-(3,3-Dimethylpyroglutamyl)-L-norleucyl-L-prolinamide (Compound 36A and 36B)

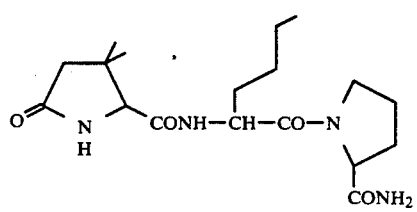

In the same manner as in Example 27, the title less polar compound 36A (175 mg) and the more polar compound 36B (120 mg) were obtained each as a powder from L-norleucyl-L-prolinamide hydrobromide (588 mg) and 3,3-dimethylpyroglutamic acid (300 mg). The compounds 36A and 36B have diastereomeric relationship to each other.

Compound 36A.

NMR (CD₃OD): δppm: 0.94 (3H, t, J=6.8Hz), 1.03 (3H, s), 1.07 (3H, s), 1.29-1.51 (4H, m), 1.58-1.76 (1H, m), 1.76-2.26 (6H, m), 2.30 (1H, d, J=16.5Hz), 3.59-3.71 (1H, m), 3.83 (1H, s), 3.84-3.96 (1H, m), 4.39 (1H, dd, J=4.8Hz and 8.2Hz), 4.62 (1H, dd, J=5.2Hz and 9.0Hz).

CIMS m/z: 367(M+1)⁺.

Compound 36B.

NMR (CD₃OD): δppm: 0.94 (3H, t, J=6.9Hz and 7.1Hz), 1.08 (3H, s), 1.26 (3H, s), 1.30-1.51 (4H, m), 1.59 1.77 (1H, m), 1.78-2.30 (6H, m), 2.36 (1H, d, J=16.4Hz), 3.58-3.72 (1H, m), 3.80 (1H, s), 3.81-3.93 (1H, m), 4.38 (1H, dd, J=4.7Hz and 8.1Hz), 4.55 (1H, dd, J=4.8Hz and 9.2Hz).

EXAMPLE 37

N-[(1R)-3-oxocyclopentanecarbonyl]-L-phenylalanyl-L-prolinamide (Compound 37)

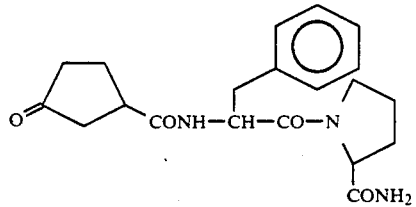

L-Phenylalanyl-L-prolinamide hydrobromide (480 mg) was dissolved in DMF (3 ml), to which was added triethylamine (0.29 ml) under cooling at −10° C. The mixture was stirred for 10 minutes under ice-cooling and the resultant precipitate was filtered off to give L-phenylalanyl-L-prolinamide in DMF solution, which was immediately used for the next reaction.

(1R)-3-Oxocyclopentanecarboxylic acid [K. Toki et al, Bull. Chem. Soc. Jpn., 31, 333 (1958)] (150 mg) was dissolved in DMF (2 ml), to which was added HOBT (216 mg), followed by cooling to 0° C. DCC (265 mg) was added thereto and the mixture was stirred at 0° C. overnight. To the mixture was added the above-mentioned L-phenylalanyl-L-prolinamide in DMF, and the mixture was stirred at 5° C. overnight. The resultant precipitate was filtered off and concentrated to dryness under reduced pressure. The residue was washed with water and purified by HP 20 column chromatography (1.0×40cm) with methanol as eluent. Further, the eluted portion was concentrated to dryness under reduced pressure, and the residue obtained was purified by silica gel column chromatography (developing solvent/chloroform:methanol:ammonia water=60:10:1) to give the title compound 37 (150 mg) as powders.

NMR (CD₃OD): δppm: 1.62-2.46 (10H, m), 2.81-3.27 (3H, m), 3.46-3.66 (1H, m), 3.70-3.91 (1H, m), 4.40-4.51 (1H, m), 7.15-7.42 (5H, m).

CIMS m/z: 372(M+1)⁺.

EXAMPLE 38

N-[(1R)-3-Oxocyclopentanecarbonyl]-L-leucyl-L-prolinamide (Compound 38)

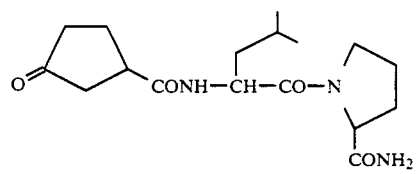

In the same manner as in Example 37, the title compound 38 (280 mg) was obtained as a powder from L-leucyl-L-prolinamide hydrobromide (675 mg) and (1R)-3-oxocyclopentanecarboxylic acid (200 mg).

NMR (CD₃OD): δppm: 0.85-1.04 (6H, m), 1.53-1.82 (3H, m), 1.85-2.45 (10H, m), 3.04-3.20 (1H, m), 3.55-3.72 (1H, m), 3.76-3.92 (1H, m), 4.33-4.48 (1H, m), 4.55-4.70 (1H, m)

CIMS m/z: 338(M+1)⁺.

EXAMPLE 39

N-(cis-2-Methyl-4-oxocyclopentanecarbonyl)-L-methionyl-L-prolinamide (Compound 39A and 39B)

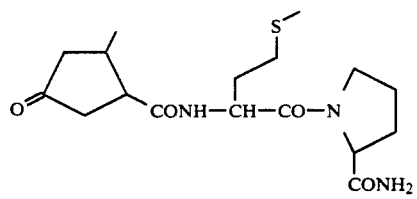

In the same manner as in Example 27, the title less polar compound 39A (152 mg) and a small amount of the more polar compound 39B were obtained as powders from L-methionyl-L-prolinamide hydrobromide (385 mg) and cis-2 -methyl-4-oxocyclopentanecarboxylic acid [K. Kojima et al, Chem. Pharm. Bull., 33, 2750 (1985)] (150 mg). The compounds 39A and 39B have diastereomeric relationship to each other.

NMR (CD₃OD): δppm: 1.01 (3H, d, J=6.9Hz), 1.83-2.50 (13H, m), 2.50-2.74 (3H, m), 3.04-3.21 (1H, m), 3.67-3.81 (1H, m), 3.83-4.02 (1H, m), 4.40 (1H, dd, J=4.6Hz and 8.2Hz), 4.78 (1H, dd, J=5.5Hz and 8.5Hz).

CIMS m/z: 370(M+1)⁺.

EXAMPLE 40

Nα-(3-Methyl 6-oxo-2 piperidinecarbonyl)-L-histidyl-L-prolinamide (Compound 40)

Using 3-methyl-6-oxo-2-piperidinecarboxylic acid (30 mg), 8 mg of the title compound was obtained in the same manner as in Example 5.

NMR (CD₃OD): ppm: 0.7-1.1 (m, 3H), 1.4-2.5 (m, 9H), 2.9-3.2 (m, 2H), 3.45 (m, 1H), 3.65 (m, 0.5H), 3.85 (m, 1H), 4.00 (m, 0.5H), 4.43 (m, 1H), 7.10 (m, 1H), 7.90 (m, 1H).

Needless to say, the present invention is not limited to these examples, and, for example, the following compounds are also encompassed in the present invention.

41. Nα-(3-Ethylpyroglutamyl)-L-histidyl-L-prolinamide

42. N$^\alpha$-(3,4-Dimethylpyroglutamyl)-L-histidyl-L-prolinamide

43. N$^\alpha$-(3-Methylpyroglutamyl)-L-histidyl-3-methyl-L-prolinamide 44. 3-[N$^\alpha$-(3-Methylpyroglutamyl)-L-histidyl]-L-5-methylthiazolidine-4-carboxamide 45. N$^\alpha$-(Tetrahydro-5-oxo-3-phenyl-3-furancarbonyl)-L-histidyl-L-prolinamide 46. 3-[N$^\alpha$-(Tetrahydro-3-methyl5-oxo-2-furancarbonyl)-L-histidyl]-L-thiazolidine-4-carboxamide 47. N$^\alpha$-(4,4-Dimethylpyroglutamyl)-L-histidyl-L-prolinamide 48. N$^\alpha$-(3-Methyl-4-ethylpyroglutamyl)-L-histidyl-L-prolinamide 49. N$^\alpha$-(3,3-Dimethyl-6-oxo-2-piperidinecarbonyl)-L-histidyl-L-prolinamide 50. 3-[N$^\alpha$-(3-Methyl-6-oxo-2-piperidinecarbonyl)-L-histidyl]-L-thiazolidine-4-carboxamide 51. N$^\alpha$-(2-Aza-3-oxospiro[4.5]decane 1-carbonyl)-L-histidyl-L-prolinamide 52. 3-[N$^\alpha$-(3-Oxocyclobutanecarbonyl)-L-histidyl]-L-thiazolidine-4-carboxamide 53. N$^\alpha$-(3-Oxocyclobutanecarbonyl)-L-histidyl-3-methyl-L-prolinamide 54. N$^\alpha$-(3-Oxocyclobutanecarbonyl)-L-histidyl-3,3-dimethyl-L-prolinamide 55. 3-[N$^\alpha$-(3-Oxocyclopentanecarbonyl)-L-histidyl]-L-5-methylthiazolidine-4-carboxamide 56. 3-[N$^\alpha$-(3-Oxocyclohexanecarbonyl)-L-histidyl]-L-5-methylthiazolidine-4-carboxamide 57. N$^\alpha$-(3-Oxocyclohexanecarbonyl)-L-histidyl-3-methyl-L-prolinamide 58. N$^\alpha$-(3-Oxocyclohexanecarbonyl)-L-histidyl-3,3-dimethyl-L-prolinamide 59. N$^\alpha$-(4-Oxo-2-phenylcyclopentanecarbonyl)-L-histidyl-L-prolinamide 60. N$^\alpha$-(6-Oxospiro[2.4]heptane-4-carbonyl)-L-histidyl-L-prolinamide 61. 3-[N$^\alpha$-(2-Methyl-4-oxocyclopentanecarbonyl)-L-histidyl]-L-thiazolidine-4-carboxamide 62. N-(3-Methyl-6-oxo-2-piperidinecarbonyl)-L-leucyl-L-prolinamide 63. N-(3-Methyl-6-oxo-2-piperidinecarbonyl)-L-methionyl-L-prolinamide 64. N-(3-Methyl-6-oxo-2-piperidinecarbonyl)-L-norleucyl-L-prolinamide 65. N-(3-Methyl-6-oxo-2-piperidinecarbonyl)-L-phenylalanyl-L-prolinamide 66. N-(3-Methyl-6-oxo-2-piperidinecarbonyl)-L-norvalyl-L-prolinamide 67. 3-[N-(3-Methylpyroglutamyl)-L-leucyl]-L-thiazolidine-4-carboxamide 68. 3-[N-(3-Methylpyroglutamyl)-L-methionyl]-L-thiazolidine-4-carboxamide 69. 3-[N-(3-Methyl-6-oxo-2-piperidinecarbonyl)-L-leucyl]-L-thiazolidine-4-carboxamide 70. 3-[N-(3-Methyl-6-oxo-2-piperidinecarbonyl)-L-methionyl]-L-thiazolidine-4-carboxamide 71. 3-[N-(3-Oxocyclopentanecarbonyl)-L-leucyl]-L-thiazolidine-4-carboxamide 72. 3-[N-(2-Methyl-4-oxocyclopentanecarbonyl)-L-methionyl]-L-thiazolidine-4-carboxamide 73. 3-[N-(2,2-Dimethyl-4-oxocyclopentanecarbonyl)-L-methionyl]-L-thiazolidine-4-carboxamide 74. N-(3-Oxocyclohexanecarbonyl)-L-leucyl-L-prolinamide 75. 3-[N-(3-Oxocyclohexanecarbonyl)-L-methionyl]-L-thiazolidine-4-carboxamide 76. N-(2-Methyl-5-oxocyclohexanecarbonyl)-L-methionyl-L-prolinamide 77. N-(3-Phenylpyroglutamyl)-L-leucyl-L-prolinamide 78. N-(3-Phenylpyroglutamyl)-L-methionyl-L-prolinamide 79. 3-[N-(3-Phenylpyroglutamyl)-L-methionyl]-L-thiazolidine-4-carboxamide 80. N-(3-Phenyl-6-oxo-2-piperidinecarbonyl)-L-leucyl-L-prolinamide 81. 3-[N-(3-Phenyl-6-oxo-2-piperidinecarbonyl)-L-methionyl]-L-thiazolidine-4-carboxamide 82. N-(3-Ethylpyroglutamyl)-L-leucyl-L-prolinamide 83. N-(3-Isopropylpyroglutamyl)-L-methionyl-L-prolinamide 84. N-(3-Ethyl-6-oxo-2-piperidinecarbonyl)-L-leucyl-L-prolinamide 85. 3-[N-(3-Ethylpyroglutamyl)-L-methionyl]-L-thiazolidine-4-carboxamide 86. N-(2-Phenyl-4-oxocyclopentanecarbonyl)-L-methionyl-L-prolinamide 87. N-(3-Methylpyroglutamyl)-L-lysyl-L-prolinamide 88. N-(3-Ethylpyroglutamyl)-L-lysyl-L-prolinamide 89. N-(3-Methylpyroglutamyl)-L-ornithyl-L-prolinamide 90. [(1S)-5-dimethylamino-1-[(2S)-2-carbamoylpyrrolidin-1-ylcarbonyl]propylcarbamoyl]-3-methylpyrrolidin-5-one 91. [(1S)-4-benzyloxycarbonylamino-1-[(2S)-2-carbamoylpyrrolidin-1-ylcarbonyl]butylcarbamoyl]-3-methylpyrrolidin-5-one 92. N-(3-Methyl-6-oxo-2-pyperidinecarbonyl)-L-lysyl-L-prolinamide 93. N-(3-Methylpyroglutamyl)-L-arginyl-L-prolinamide 94. N-(3-Methylpyroglutamyl)-L-threonyl-L-prolinamide 95. [(1S)-2-Methoxy-1-[(2S)-2-carbamoylpyrrolidin-1-ylcarbonyl]propylcarbamoyl]-3-methylpyrrolidin-5-one 96. N-(3-Methylpyroglutamyl)-L-cysteyl-L-prolinamide 97. [(1S)-2-Methylthio-1-[(2S)-2-carbamoylpyrrolidin-1-ylcarbonyl]ethylcarbamoyl]-3-methylpyrrolidin-5-one 98. [(1S)-2-Phenylthio-1-[(2S)-2-carbamoylpyrrolidin-1-ylcarbonyl]ethylcarbamoyl]-3-methylpyrrolidin-5-one 99. [(1S)-2-Methylsulfonyl-1-[(2S)-2-carbamoylpyrrolidin-1-ylcarbonyl]ethylcarbamoyl]-3-methylpyrrolidin-5-one 100. N-(3-Methylpyroglutamyl)-L-asparagyl-L-prolinamide 101. N-(3-Methylpyroglutamyl)-L-tyrosyl-L-prolinamide 102. N-(3-Methyl-6-oxo-2-piperidinecarbonyl)-L-seryl-L-prolinamide 103. N-(2-Methyl-4-oxocyclopentanecarbonyl)-L-seryl-L-prolinamide 104. N-(2-Methyl-5-oxocyclohexanecarbonyl)-L-threonyl-L-prolinamide 105. N-(3-Ethyl-6-oxo-2-piperidinecarbonyl)-L-asparagyl-L-prolinamide 106. N-(3,3-dimethylpyroglutamyl)-L-arginyl-L-prolinamide 107. [(1S)-4-Acetylamino-1-[(2S)-2-carbamoylpyrrolidin-1-ylcarbonyl]butylcarbamoyl]-3-methylpyrrolidin-5-one 108. [(1S)-2-Acetylamino-1-[(2S)-2-carbamoylpyrrolidin-1-ylcarbonyl]butylcarbamoyl]-3-methylpyrrolidin-5-one The evaluation tests for anti-reserpine action, anti-chlorpromazine action and spinal reflex stimulant action were conducted as regards the compounds of the present invention.

For comparison, the same tests were conducted also as regards TRH and the hitherto-known DN1417 of the following formula:

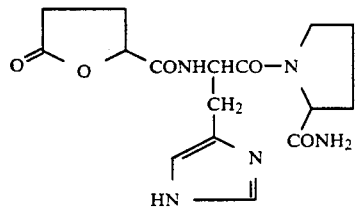

TEST EXAMPLE 1

Anti-Reserpine Action (Antagonistic Action Against Hypothermia)

ICR male mice weighing 35-40 g were subcutaneously administered with reserpine at the dose of 5 mg/kg. About 2 hours later, each of the mice was held by a mouse-holder, and a body temperature sensor was intrarectally inserted. Thereafter, the body temperature was automatically measured every 10 minutes. The test compound dissolved in saline was subcutaneously administered 3 or 3.5 hours after administration of reserpine. After the administration of the test compound, the body temperature was measured every 10 minutes over the period of 120 minutes. The area below the body temperature line during the period was calculated, from which the regression line was estimated based upon least square method, and estimated was the amount of the test compound necessary for raising the body temperature by 1° C. on the average for 120 minutes from that just before the administration of the test compound (Table 1).

TABLE 1

| | Concentration of test compound necessary for raising body temperature by 1° C. on the average for 120 minutes (mg/kg, SC) |
|---|---|
| TRH | 2.52 |
| DN1417 | 2.06 |
| Compound 1 | 0.30 |
| Compound 2 | 1.11 |
| Compound 3 | 0.20 |
| Compound 4 | 0.34 |
| Compound 5 | 0.12 |
| Compound 10 | 0.53 |
| Compound 11 | 0.28 |
| Compound 13 | 0.71 |
| Compound 16 | 0.12 |
| Compound 19 | 0.14 |
| Compound 20 | 0.27 |
| Compound 21 | 0.18 |
| Compound 27A | 0.18 |
| Compound 28A | 0.48 |
| Compound 29A | 0.91 |
| Compound 31A | 0.33 |

TEST EXAMPLE 2

Anti-Chlorpromazine Action (Locomotor Stimulant Action)

ICR male mice weighing 35-40 g (four animals per group) were subcutaneously administered with chlorpromazine.HCl at the dose of 5 mg/kg and immediately set in the automatic locomotor-measuring apparatus (AUTOMEX). One hour later, the test compound dissolved in saline was subcutaneously administered, and the locomotor activity was measured every 15 minutes for 120 minutes. The total locomotor activity during the period of 120 minutes was calculated and the regression line was estimated based on the method of least squares, from which the amount of the test compound necessary for inducing 3000 locomotor-count was estimated (Table 2).

TABLE 2

| | Concentration of test compound necessary for inducing 3000 count of automatism quantity in 2 hours (mg/kg. SC) |
|---|---|
| TRH | 6.82 |
| DN1417 | 4.34 |
| Compound 1 | 0.51 |
| Compound 2 | 12.94 |
| Compound 3 | 0.47 |
| Compound 4 | 0.63 |
| Compound 5 | 0.70 |
| Compound 10 | 1.89 |
| Compound 11 | 1.89 |
| Compound 13 | 1.03 |
| Compound 16 | 0.88 |
| Compound 19 | 0.54 |
| Compound 20 | 1.30 |
| Compound 21 | 0.83 |
| Compound 27A | 2.63 |
| Compound 28A | 1.64 |
| Compound 31A | 16.30 |

TEST EXAMPLE 3

Flexor Reflex in Spinalized Rats

Wistar male rats (weighing 450-520 g) were anesthetized with ether, and the cervical part of spinal cord was exposed, into which a tracheal cannula was inserted. The vagus nerves were severed bilaterally at the cervical region. Thereafter, the cervical vertebra C1 segment was transected, and rapidly, artificial ventilation was given with the use of an artificial respirator (Shinano Factory 60 rpm. 4 ml/stroke). The rat was placed on a thermostated apparatus in which water thermostated at 37° C. was circulated and fixed thereto at forelimbs, right hindlimb, tooth and tail. A venous cannula was inserted into the femoral vein in the right hindlimb and two needle electrodes were subcutaneously inserted into the left skin of the toe, and a piece of thread was attached to the limb with the edge of the thread bonded to a force-displacement transducer. Tension of about 5 g was applied to the thread. Through the electrodes, electric stimuli of 50-100 V were applied once per 30 seconds. The flexor reflex was recorded on the polygraph via a force-displacement transducer. After the reaction became constant in about one-hours' lapse for stabilization, the test compound dissolved in saline was intravenously administered. Thereafter, the reaction was recorded for 1 hour. In the data, taking the mean of the three reactions just before administration of the test compound for 100%, the reflex amplitude at 1-, 3-, 5-, 8-, 10-, 15-, 20-, 30-, 40-, 50- and 60-minutes' lapse after administration of the test compound were calculated. In Table 3, there are shown calculated area below the straight line linking the obtained reflex amplitude at the respective above-mentioned time covering 60 minutes in the case of administration of each test compounds at the dose of 0.1 mg/kg, and the reflex amplitude at 10- and 60-minutes' lapse after administration (Table 3).

TABLE 3

| | Intavenous administration at the dose of 0.1 mg/kg | | |
|---|---|---|---|
| | Area below the reflex amplitude linking line | Reflex amplitude (%) | |
| | | 10 min. after | 60 min. after |
| Saline | 6047 | 104.1 | 93.3 |
| TRH | 6418 | 117.7 | 79.3 |
| DN1417* | 8152 | 113.7 | 162.8 |
| Compound 1 | 12970 | 159.3 | 298.1 |
| Compound 2 | 7077 | 126.1 | 106.6 |
| Compound 3 | 13811 | 190.5 | 277.6 |
| Compound 4 | 9404 | 142.8 | 163.9 |
| Compound 5 | 9221 | 131.6 | 168.3 |
| Compound 10 | 16593 | 242.7 | 329.2 |
| Compound 11 | 11321 | 140.4 | 240.8 |
| Compound 13 | 8572 | 110.4 | 167.2 |
| Compound 16 | 12016 | 151.7 | 252.3 |
| Compound 19 | 11860 | 138.4 | 246.4 |
| Compound 20 | 6317 | 104.8 | 107.0 |
| Compound 21 | 7186 | 114.8 | 144.9 |
| Compound 19* | 19114 | 250.5 | 339.9 |
| Compound 20* | 10355 | 128.8 | 222.6 |
| Compound 21* | 14294 | 170.1 | 274.2 |
| Compound 27A | 8769 | 126.1 | 156.0 |
| Compound 28A | 9188 | 125.1 | 195.3 |
| Compound 29A* | 7063 | 124.4 | 120.7 |
| Compound 31A | 8126 | 130.0 | 129.3 |
| Compound 33A* | 7172 | 118.9 | 119.9 |
| Compound 37A* | 5868 | — | — |

*The results at the dose of 0.3 mg/kg are indicated.

The hormone activity of every compound of the invention was found to be as equal to or less than that of TRH by colloid formation test in thyroid follicles.

What is claimed is:

1. A peptide derivative of the following formula

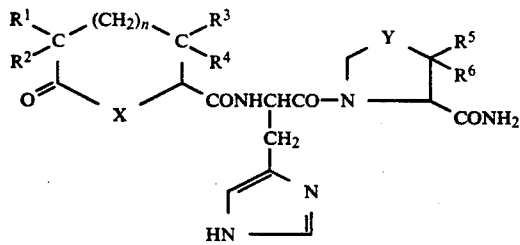

wherein $R^1$ and $R^2$ are the same or different and respectively means a hydrogen atom or a $C_{1-5}$ alkyl group, $R^3$ and $R^4$ are the same or different and respectively mean a hydrogen atom or a $C_{1-5}$ alkyl group or phenyl, or $R^3$ and $R^4$ combinedly means a $C_{2-7}$ alkylene group, $R^5$ and $R^6$ are the same or different and respectively mean a hydrogen atom or a $C_{1-5}$ alkyl group, X means —NH— or —O—, Y means —CH$_2$— or —S—, and n means 0 or 1, provided that all of $R^1$, $R^2$, $R^3$ and $R^4$ do not mean hydrogen atoms at the same time, or a pharmaceutically acceptable acid addition salt thereof.

2. A peptide derivative of the following formula

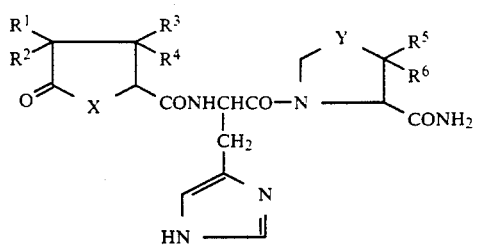

wherein $R^1$, $R^2$, $R^3$, $R^4$, $R^5$, $R^6$, X and Y are of the same meaning as defined in claim 1, provided that all of $R^1$, $R^2$, $R^3$ and $R^4$ do not mean a hydrogen atom at the same time, or a pharmaceutically acceptable acid addition salt thereof as claimed in claim 1.

3. A peptide derivative or a pharmaceutically acceptable acid addition salt thereof as claimed in claim 1, which is selected from the group consisting of $N^\alpha$-(cis-3-methylpyroglutamyl)-L-histidyl-L-prolinamide, $N^\alpha$-(trans-3-methylpyroglutamyl)-L-histidyl-L-prolinamide, 3-[$N^\alpha$-(cis-3-methylpyroglutamyl)-L-histidyl]-L-thiazolidine-4-carboxamide, 3-[$N^\alpha$-(trans-3-methylpyroglutamyl)-L-histidyl]-L-thiazolidine-4-carboxamide, $N^\alpha$-[(2R,3R)-tetrahydro-3-methyl-5-oxo-2-furancarbonyl]-L-histidyl-L-prolinamide, $N^\alpha$-[(2S,4R)-tetrahydro-4-methyl-5-oxo-2-furancarbonyl]-L-histidyl-L-prolinamide, $N^\alpha$-(4-methylpyroglutamyl)-L-histidyl-L-prolinamide, $N^\alpha$-(3,3-dimethylpyroglutamyl)-L-histidyl-L-prolinamide, 3-[$N^\alpha$-(3,3-dimethylpyroglutamyl)-L-histidyl]-L-thiazolidine-4-carboxamide, $N^\alpha$-(trans-3-phenylpyroglutamyl)-L-histidyl-L-prolinamide, $N^\alpha$-(cis-3-phenylpyroglutamyl)-L-histidyl-L-prolinamide, 3-[$N^\alpha$-(cis-3-ethylpyroglutamyl)-L-histidyl]-L-thiazolidine-4-carboxamide and $N^\alpha$-(cis-3-methylpyroglutamyl)-L-histidyl-3,3-dimethylprolinamide, 3-[$N^\alpha$-(2-aza-3-oxospiro[4.5]decane-1-carbonyl)-L-histidyl]-L-thiazolidine-4-carboxamide and $N^\alpha$-(3-methyl-6-oxo-2-piperidinecarbonyl)-L-histidyl-L-prolinamide.

4. A peptide derivative of the following formula

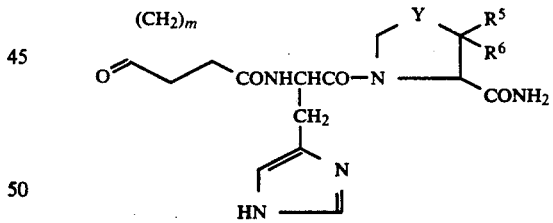

wherein $R^5$ and $R^6$ are the same or different and respectively mean a hydrogen atom or a $C_{1-5}$ alkyl group, m is an integer of 1-3 and Y means —CH$_2$— or —S—, or a pharmaceutically acceptable acid addition salt thereof.

5. A peptide derivative or a pharmaceutically acceptable acid addition salt thereof as claimed in claim 4, which is selected from the group consisting of $N^\alpha$-(3-oxocyclobutanecarbonyl)-L-histidyl-L-prolinamide, $N^\alpha$-(3-oxocyclopentanecarbonyl)-L-histidyl-L-prolinamide, $N^\alpha$-(3-oxocyclohexanecarbonyl)-L-histidyl-L-prolinamide, 3-[$N^\alpha$-(3-oxocyclohexanecarbonyl)-L-histidyl]-L-thiazolidine-4-carboxamide, $N^\alpha$-[(1R)-3-oxocyclopentanecarbonyl]-L-histidyl-L-prolinamide, 3-[$N^\alpha$-(3-oxocyclopentanecarbonyl)-L-histidyl]-L-thiazolidine-4-carboxamide and $N^\alpha$-[(1R)-3-oxocyclopentanecarbonyl]-L-histidyl- 3,3-dimethyl-prolinamide.

6. A peptide derivative of the formula

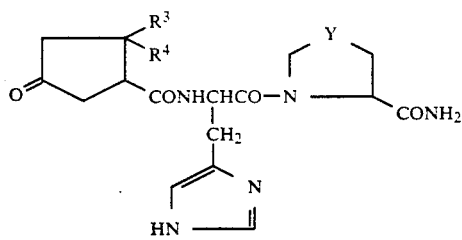

wherein Y means —CH$_2$— or —S—, R$^3$ and R$^4$ are the same or different and respectively means a hydrogen atom or a C$_{1-5}$ alkyl group or phenyl, or R$^3$ and R$^4$ combinedly means a C$_{2-7}$ alkylene group, provided that R$^3$ and R$^4$ do not means a hydrogen atom at the same time, or a pharmaceutically acceptable acid addition salt thereof.

7. A peptide derivative or a pharmaceutically acceptable acid addition salt thereof as claimed in claim 6, which is selected from the group consisting of N$^\alpha$-(cis-2-methyl-4-oxocyclopentanecarbonyl)-L-histidyl-L-prolinamide, N$^\alpha$-(trans-2-methyl-4-oxocyclopentanecarbonyl)-L-histidyl-L-prolinamide, N$^\alpha$-(2,2-dimethyl-4-oxocyclopentanecarbonyl)-L-histidyl-L-prolinamide, N$^\alpha$-(cis-2-ethyl-4-oxocyclopentanecarbonyl-L-histidyl-L-prolinamide and N$^\alpha$-(3-oxospiro[4.5]-decane-1-carbonyl)-L-histidyl-L-prolinamide.

8. A peptide derivative of the formula

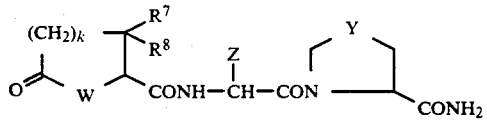

wherein R$^7$ and R$^8$ are the same or different and respectively means a hydrogen atom, a C$_{1-5}$ alkyl group or phenyl, W is —NH— or —CH$_2$—, Z is a hydrogen atom, a benzyl group wherein phenyl may be substituted by hydroxyl, or a C$_{1-5}$ alkyl group which may be substituted by —SH, —SR$^9$, —SO$_2$R$^9$, —CONH$_2$,

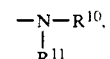

—OR$^{12}$ or

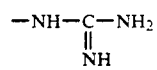

(where R$^9$ is a C$_{1-5}$ alkyl group or an aryl group, R$^{10}$ and R$^{11}$ are the same or different and respectively mean a hydrogen atom, a C$_{1-5}$ alkyl group or an amino protecting group and R$^{12}$ is a hydrogen atom, a C$_{1-5}$ alkyl group or a hydroxyl protecting group), Y is —CH$_2$— or —S—, and k is 1 or 2, provided that when W is —NH—, R$^7$ and R$^8$ are not hydrogen atoms at the same time, or a pharmaceutically acceptable acid addition salt thereof.

9. A peptide derivative or a pharmaceutically acceptable acid addition salt thereof as claimed in claim 8, wherein k is 1.

10. A peptide derivative or a pharmaceutically acceptable acid addition salt thereof as claimed in claim 8, wherein Z is a C$_{1-5}$ alkyl which may be substituted by —SR$^9$ (wherein R$^9$ is as defined in claim 9) or a benzyl group.

11. A peptide derivative or a pharmaceutically acceptable acid addition salt thereof as claimed in claim 8, which is selected from the group consisting of N-(cis-3-methylpyroglutamyl)-L-leucyl-L-prolinamide, N-(cis-3-methylpyroglutamyl)-L-methionyl-L-prolinamide, N-(cis-3-methylpyroglutamyl)-L-norvalyl-L-prolinamide, N-(cis-3-methylpyroglutamyl)-L-phenylalanyl-L-prolinamide, N-(cis-3-methylpyroglutamyl)-L-norleucyl-L-prolinamide, N-(cis-3,3-dimethylpyroglutamyl)-L-leucyl-L-prolinamide, N-(cis-3,3-dimethylpyroglutamyl)-L-norvalyl-L-prolinamide, N-(cis-3,3-dimethylpyroglutamyl)-L-methionyl-L-prolinamide, N-(cis-3,3-dimethylpyroglutamyl)-L-phenylalanyl-L-prolinamide, N-(cis-3,3-dimethylpyroglutamyl)-L-norleucyl-L-prolinamide, N-[(1R)-3,3-oxocyclopentanecarbonyl)-L-phenylalanyl-L-prolinamide, N-[(1R)-3,3-oxocyclopentanecarbonyl)-L-leucyl-L-prolinamide and N-(cis-2-methyl-4-oxocyclopentanecarbonyl)-L-methionyl-L-prolinamide.

* * * * *

UNITED STATES PATENT AND TRADEMARK OFFICE
CERTIFICATE OF CORRECTION

PATENT NO. : 5,151,497
DATED : September 29, 1992
INVENTOR(S) : Uchida et al.

It is certified that error appears in the above-identified patent and that said Letters Patent is hereby corrected as shown below:

Title page, item [30], please insert the following foreign application priority data:

-- Feb. 21, 1989 [JP] Japan..... 1-39457
   Nov. 15, 1989 [JP] Japan..... 1-294836
   May  2, 1989 [JP] Japan..... 1-112244
   Nov. 2, 1989 [JP] Japan..... 1-284803
   Dec. 15, 1989 [JP] Japan..... 1-323782 --

Column 2, lines 30-35,

" 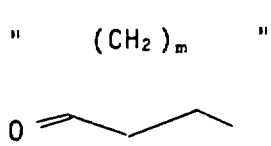 "    should read -- 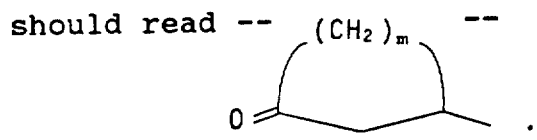 .

Column 2, lines 23, 24, 41, 55, 57, 58 and 68, "means" should read -- mean --.

Column 5, lines 1-5,

" 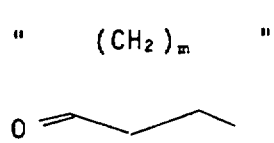 "    should read -- 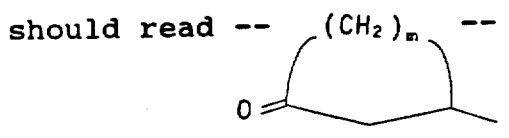 .

Column 5, line 47, "[1']" should read -- [I'] --.

Column 5, line 54, "I'" should read -- [I'] --.

UNITED STATES PATENT AND TRADEMARK OFFICE
CERTIFICATE OF CORRECTION

PATENT NO. : 5,151,497

DATED : September 29, 1992

INVENTOR(S) : Uchida et al.

It is certified that error appears in the above-identified patent and that said Letters Patent is hereby corrected as shown below:

Column 8, line 63, "[II'" should read -- [II'] --.
Column 9, lines 1-5,

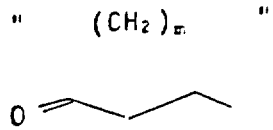   should read -- 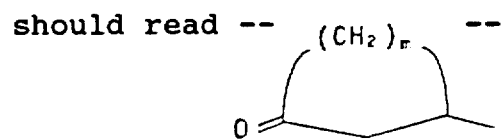 --.

Column 9, lines 13-15,

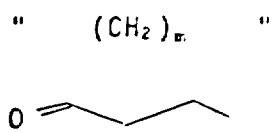   should read -- 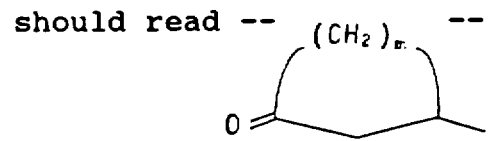 --.

Column 9, lines 26-30,

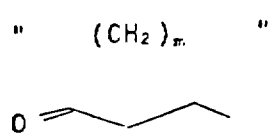   should read -- 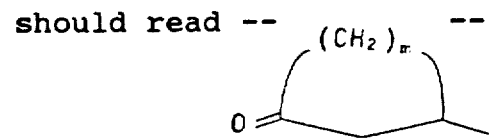 --.

Column 9, line 68, "[VII]" should read -- [XIII] --.

UNITED STATES PATENT AND TRADEMARK OFFICE
CERTIFICATE OF CORRECTION

PATENT NO. : 5,151,497

DATED : September 29, 1992

INVENTOR(S) : Uchida et al.

It is certified that error appears in the above-identified patent and that said Letters Patent is hereby corrected as shown below:

Column 10, line 28, "[IV]" should read -- [XV] --.

Column 12, line 34, "cyclohexylidenemmalonate" should read -- cyclohexylidenemalonate --.

Column 12, line 54, "IR$\gamma$" should read -- IR$\upsilon$ --.

Column 13, line 10, delete "m.p.146° -147°C".

Column 13, line 13, insert -- m.p.146° - 147°C --.

Column 13, line 15, "-4-carboethoxy-1" should read -- -4-carboethoxy-1- --.

Column 13, line 40, "IR$\gamma$" should read -- IR$\upsilon$ --.

Column 13, line 43, "-1-carboxy-3 oxospiro" should read -- -1-carboxy-3-oxospiro --.

Column 13, line 55, "IR$\gamma$" should read -- IR$\upsilon$ --.

Column 14, line 4, "IV$\gamma$" should read -- IR$\upsilon$ --.

Column 14, line 36, "J=6Hz)" should read -- J=6Hz --.

Column 14, line 37, "J=4Hz)" should read -- J=4Hz --.

Column 14, line 44, "<10°C" should read -- -10°C --.

Column 16, line 40, "-2 furanocarbonyl" should read -- -2-furanocarbonyl --.

UNITED STATES PATENT AND TRADEMARK OFFICE
CERTIFICATE OF CORRECTION

PATENT NO. : 5,151,497

DATED : September 29, 1992

INVENTOR(S) : Uchida et al.

It is certified that error appears in the above-identified patent and that said Letters Patent is hereby corrected as shown below:

Column 16, line 48, "4.95 5.04" should read -- 4.95-5.04 --.

Column 17, line 7, "(2 ()" should read -- (2 1) --.

Column 20, line 42, "3-oxocyclopentane-carboxylic" should read -- 3-oxocyclopentanecarboxylic --.

Column 21, line 19, "cis-2-methyl-4 ox-" should read -- cis-2-methyl-4-ox- --.

Column 21, line 21, "dihydrobromide acid" should read -- dihydrobromide --.

Column 22, line 17, "(M.2)$^+$" should read -- (M+2)$^+$ --.

Column 22, line 38, "3[N$^\alpha$-(cis-3-" should read -- 3-[N$^\alpha$-(cis-3- --.

Column 27, line 33, "(CD$_3$OR)" should read -- (CD$_3$OD) --.

Column 29, line 23, "N-[(1R)-3-oxocyclo" should read -- N-[(1R)-3-Oxocyclo --.

Column 30, line 54, "-(3-Methyl 6-oxo-2" should read -- -(3-Methyl-6-oxo-2- --.

Column 31, line 19, "[4.5]decane 1-carbonyl" should read -- [4,5]decane-1-carbonyl --.

Column 31, line 21, "-L-histidyl)" should read -- -L-histidyl] --.

UNITED STATES PATENT AND TRADEMARK OFFICE
CERTIFICATE OF CORRECTION

PATENT NO. : 5,151,497

DATED : September 29, 1992

INVENTOR(S) : Uchida et al.

It is certified that error appears in the above-identified patent and that said Letters Patent is hereby corrected as shown below:

Column 32, line 28, "[(1S)-5-dimethyl" should read -- [(1S)-5-Dimethyl --.

Column 32, line 31, "[(1S)-4-benzyloxy" should read -- [(1S)-4-Benzyloxy --.

Column 32, line 67, "N-(3,3-dimethyl" should read -- N-(3,3-Dimethyl --.

Column 36, line 26, "[(2R,3R)" should read -- [(2S,3R) --.

Column 36, lines 41-45,

"    (CH₂)ₙ    "

should read --

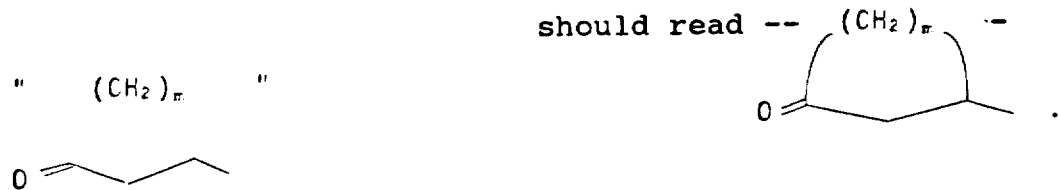

.

Column 37, line 18, "means" should read -- mean --.

Column 38, lines 37, 38, 39-40, 40-41 and 42, "cis-3,3-dimethyl" should read -- 3,3-dimethyl --.

UNITED STATES PATENT AND TRADEMARK OFFICE
CERTIFICATE OF CORRECTION

PATENT NO. : 5,151,497
DATED : September 29, 1992
INVENTOR(S) : Uchida et al

It is certified that error appears in the above-indentified patent and that said Letters Patent is hereby corrected as shown below:

Column 38, lines 43 and 44, "3,3-oxo" should read --3-oxo--

Signed and Sealed this

First Day of March, 1994

Attest:

BRUCE LEHMAN

*Attesting Officer*   *Commissioner of Patents and Trademarks*